(12) United States Patent
Borjigin et al.

(10) Patent No.: US 9,918,651 B2
(45) Date of Patent: Mar. 20, 2018

(54) ELECTROCARDIOGRAM DATA ANALYSIS METHOD FOR RAPID DIAGNOSIS

(71) Applicant: THE REGENTS OF THE UNIVERSITY OF MICHIGAN, Ann Arbor, MI (US)

(72) Inventors: Jimo Borjigin, Ann Arbor, MI (US); Duan Li, Ann Arbor, MI (US)

(73) Assignee: THE REGENTS OF THE UNIVERSITY OF MICHIGAN, Ann Arbor, MI (US)

(*) Notice: Subject to any disclaimer, the term of this patent is extended or adjusted under 35 U.S.C. 154(b) by 82 days.

(21) Appl. No.: 14/843,483

(22) Filed: Sep. 2, 2015

(65) Prior Publication Data

US 2016/0058318 A1 Mar. 3, 2016

Related U.S. Application Data

(60) Provisional application No. 62/044,747, filed on Sep. 2, 2014.

(51) Int. Cl.
*A61B 5/04* (2006.01)
*A61B 5/0402* (2006.01)
(Continued)

(52) U.S. Cl.
CPC ........ *A61B 5/04015* (2013.01); *A61B 5/0402* (2013.01); *A61B 5/04018* (2013.01); *A61B 5/7275* (2013.01); *A61B 5/044* (2013.01)

(58) Field of Classification Search
CPC . A61B 5/04015; A61B 5/7275; A61B 5/0402; A61B 5/04018; A61B 5/044
See application file for complete search history.

(56) References Cited

U.S. PATENT DOCUMENTS 6,132,381 A 10/2000 Forbes et al.
6,409,659 B1 6/2002 Warner et al.
(Continued)

FOREIGN PATENT DOCUMENTS

EP 2030565 A1 3/2009

OTHER PUBLICATIONS

International preliminary report on patentability from PCT/US2015/048065 dated Mar. 16, 2017.
(Continued)

*Primary Examiner* — Rex R Holmes
(74) *Attorney, Agent, or Firm* — Marshall, Gerstein & Borun LLP

(57) ABSTRACT

Periodic electrical signal data, such as electrocardiogram signal data, is collected, analyzed, and transformed into compacted, multi-dimensional matrix that makes it easier for healthcare professionals to analyze the health condition of a patient. The electrical signal data, characterized by periodic deflection elements that collectively form a periodic signal complex, is analyzed to determine peaks of deflection elements, where peaks can vary greatly, but in ways not readily visible on standard electrocardiograms. The techniques create and display the multi-dimensional matrix from aligning identified peaks, so that the matrix can be readily overlayed with an automatically-identified signal pattern indicative of one or more of an arrhythmia, a precursor to an arrhythmia, a cardiac event, and/or a precursor to a cardiac even.

19 Claims, 40 Drawing Sheets
(37 of 40 Drawing Sheet(s) Filed in Color)

(51) Int. Cl.
*A61B 5/00* (2006.01)
*A61B 5/044* (2006.01)

(56) References Cited

U.S. PATENT DOCUMENTS

| | | |
|---|---|---|
| 7,113,820 B2 | 9/2006 | Schlegel et al. |
| 2003/0135097 A1 | 7/2003 | Wiederhold et al. |
| 2004/0073098 A1 | 4/2004 | Geva et al. |
| 2004/0193064 A1 | 9/2004 | Shusterman |
| 2009/0112106 A1 | 4/2009 | Zhang |
| 2009/0112110 A1 | 4/2009 | Zhang |
| 2011/0021936 A1 | 1/2011 | Luo |
| 2013/0046021 A1 | 2/2013 | Rubinstein et al. |
| 2014/0128758 A1* | 5/2014 | Galloway ............ A61B 5/7203 600/518 |

OTHER PUBLICATIONS

International search report and written opinion from Application No. PCT/US2015/48065 dated Dec. 4, 2015.

Gladstone et al., "Atrial fibrillation in patients with cryptogenic stroke," N Engl J Med 370: 2467-2477 (2014).
Goldberger et al., "Physiobank, physiotoolkit, and physionet: Components of a new research resource for complex physiologic signals," Circulation 101: e215-e220 (2000).
Kew et al., "Variable threshold method for ECG R-peak detection," J Med Syst 35: 1085-1094 (2011).
Li et al., "Electrocardiomatrix: A new method for beat-by-beat visualization and inspection of cardiac signals," J Integr Cardiol 1(5):124-128 (2015).
Moody et al., "The impact of the MIT-BIH arrhythmia database," IEEE Eng Med Biol Mag 20: 45-50 (2001).
Riera et al., "The enigmatic sixth wave of the electrocardiogram: the U wave," Cardiol J 15: 408-421 (2008).
Ritter, "Holter in monitoring of cardiac pacing," Prog Cardiovasc Dis 56:211-223 (2013).
Rosero et al., "Ambulatory ECG monitoring in atrial fibrillation management," Prog Cardiovasc Dis 56:143-152 (2013).
Sanna, et al., "Cryptogenic stroke and underlying atrial fibrillation," N Engl J Med 370: 2478-2486 (2014).
Yong et al., "The electrocardiogram at a crossroads," Circulation 128: 79-82 (2013).

* cited by examiner

Matrix formation
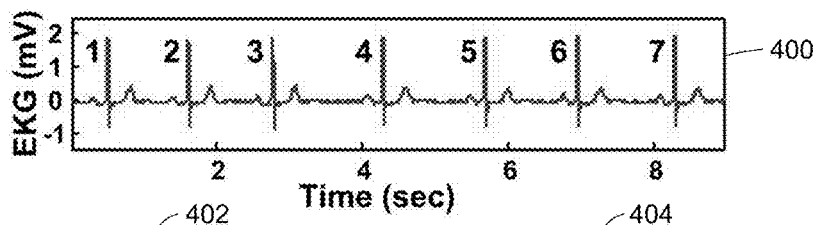
FIG. 6A
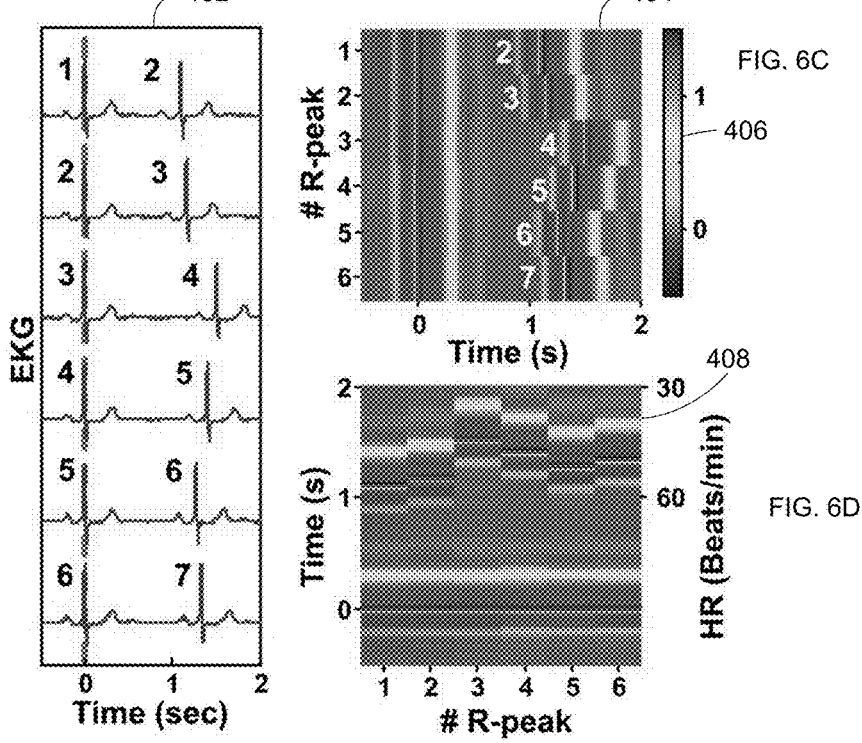
FIG. 6B
FIG. 6C
FIG. 6D

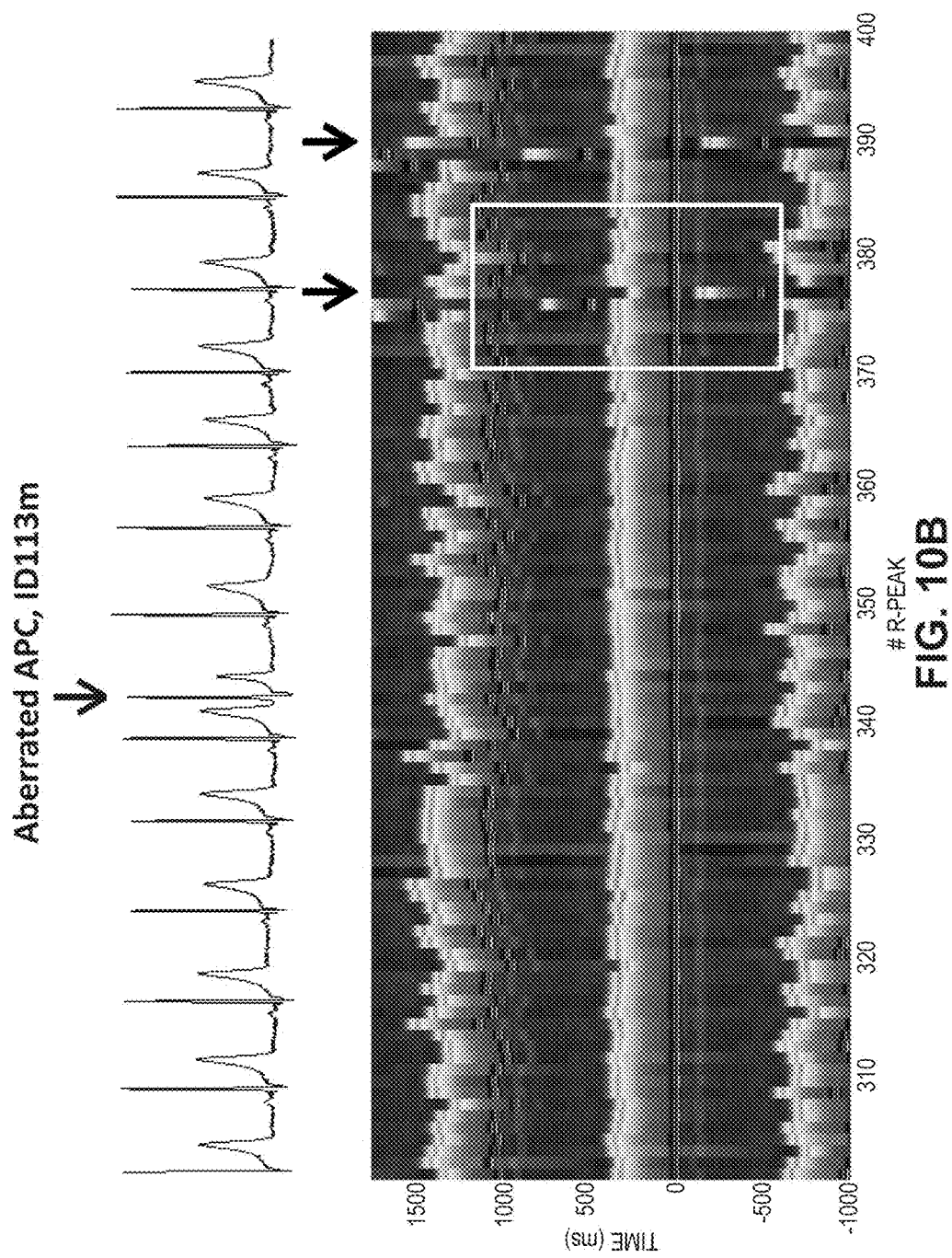

ELECTROCARDIOGRAM DATA ANALYSIS METHOD FOR RAPID DIAGNOSIS

CROSS-REFERENCE TO RELATED APPLICATION

This application claims the priority benefit under 35 U.S.C. § 119(e) of U.S. Provisional Patent Application No. 62/044,747, filed Sep. 2, 2014, the disclosure of which is incorporated herein by reference in its entirety.

FIELD OF THE DISCLOSURE

The present disclosure relates generally to techniques for analyzing periodic electrical signal data of the cardiac, muscular, or brain activity of a subject and, more particularly, to techniques for analyzing such electrical signal data to create a multi-dimensional matrix showing changes over time.

BACKGROUND

The background description provided herein is for the purpose of generally presenting the context of the disclosure. Work of the presently named inventor, to the extent it is described in this background section, as well as aspects of the description that may not otherwise qualify as prior art at the time of filing, are neither expressly nor impliedly admitted as prior art against the present disclosure.

Physicians and healthcare professionals rely on electrical signal data from patients to assess various types of activities. Electrocardiogram (ECG or EKG) data records electrical activity of the heart. Electroencephalography (EEG) data records electrical activity of the brain, measured along the scalp. Electromyography (EMG) data records electrical activity of skeletal muscles. The techniques for displaying such electrical signal data are uniform, but fairly old. The signal data is plotted in time measured fashion, with electrical activity on one axis and time on the other. Physicians and healthcare professionals trained in analyzing the data can analyze and diagnose some physical conditions of a patient, but to do so they often must examine long reams of data and even then some diagnostic indicators can go undetected. This is especially true for indicators of physiologic states that are either (i) long-term indicators (i.e., they develop over long periods of signal measurement) or (ii) subtle indicators, which are often masked by the data and may appear as noise or a signal anomaly.

There is a need for a better, more effective way of analyzing and displaying electrical signal data.

SUMMARY OF THE INVENTION

In accordance with an embodiment, a method of analyzing periodic electrical signal data of cardiac, muscular, or brain activity, wherein the electrical signal data is characterized by periodic deflection elements that collectively form a periodic signal complex, the method comprises: collecting the electrical signal data over a sampling window of time; automatically detecting, using a signal detection module, periodic localized peaks for one of the deflection elements from the electrical signal data and over the sampling window of time; determining, in the signal detection module, a relative peak value for each of the periodic localized peaks over the sampling window of time; transforming, using a matrix generating module, the electrical signal data into a time-complex matrix, the time-complex matrix characterized by alignment of each of the periodic localized peaks at a zero time level, wherein the respective relative peak values for the periodic localized peaks is represented by an intensity scale at the zero time level, and wherein the time-complex matrix is characterized by representing changes in the temporal spacing and intensities of the periodic signal complexes over the sampling window; and displaying the time-complex matrix as either a horizontal time progression or a vertical time progression plot.

In some examples, the periodic electrical signal data is selected from one of electrocardiogram (EKG) data, electromyography (EMG) data, and electroencephalography (EEG) data.

In some examples, the periodic electrical signal data is EKG data, and wherein the periodic signal complex is a QRS complex comprising, as the periodic deflection elements, P elements, Q elements, R elements, S elements, and T elements.

In some examples, automatically detecting periodic localized peaks for one of the deflection elements includes automatically detecting, using the signal detection module, R element peaks in the EKG data and performing a validation on the R elements peaks to identify and correct any mis-detected R element peaks in the EKG data.

In some examples, the method includes analyzing the time-complex matrix to identify patterns in the periodic deflection elements over the sampling window, and from the analysis of the time-complex matrix, automatically detecting a pattern indicative of one or more of an arrhythmia, a precursor to an arrhythmia, a cardiac event, and/or a precursor to a cardiac event.

In some examples, the method includes automatically detecting the pattern indicative of at least one of atrial premature contraction (APC), aberrated APC, blocked APC, supraventricular tachycardia, atrial flutter, atrial fibrillation, junctional tachycardia, premature ventricular contraction (PVC), interpolated PVC, ventricular bigeminy, ventricular trigeminy, ventricular couplets, ventricular tachycardia, 2nd degree (Mobitz I and Mobitz II) heart block, 3rd degree (or complete) heart block, heart block followed by atrial tachycardia (AT), and heart block followed by atrial fibrillation (AF).

In some examples, the periodic electrical signal data is EKG data, and wherein the periodic signal complex is a QRS complex comprising, as the periodic deflection elements, P elements, Q elements, R elements, S elements, and T elements, wherein the method comprises automatically detecting the pattern indicative of at least one of RR interval changes, left bundle branch blockage, right bundle branch blockage, ST depression, ST elevation, QT interval changes, QRS interval changes, PR interval changes, split P-waves, and widened QRS bases indicative of Wolff-Parkinson-White heart beats.

In accordance with an embodiment, a system comprises: a processor and a memory, the memory storing instructions that when executed by the processor, cause the processor to: collect electrical signal data over a sampling window of time, wherein the electrical signal data is data of cardiac, muscular, or brain activity, and wherein the electrical signal data is characterized by periodic deflection elements that collectively form a periodic signal complex; detect periodic localized peaks for one of the deflection elements from the electrical signal data and over the sampling window of time; determine a relative peak value for each of the periodic localized peaks over the sampling window of time; transform the electrical signal data into a time-complex matrix, the time-complex matrix characterized by alignment of each of the periodic localized peaks at a zero time level, wherein the respective relative peak values for the periodic localized peaks is represented by an intensity scale at the zero time level, and wherein the time-complex matrix is characterized by representing changes in the temporal spacing and intensities of the periodic signal complexes over the sampling window; and optionally display the time-complex matrix as either a horizontal time progression or a vertical time progression plot.

In accordance with an embodiment, a method of detecting patterns in periodic electrical signal data of cardiac, muscular, or brain activity, the method comprises: receiving a time-complex matrix developed from the periodic electrical signal data, the time-complex matrix being characterized by having an alignment of periodic localized peaks of deflection elements identified over a sampling window of time, wherein each of the periodic localized peaks over the sampling window of time are aligned at a zero time level, wherein the respective relative peak values for the periodic localized peaks are represented by an intensity scale at the zero time level, and wherein the time-complex matrix is characterized by representing changes in the temporal spacing and intensities of the periodic signal complexes over the sampling window; analyzing the time-complex matrix to identify patterns in the periodic deflection elements over the sampling window; and from the analysis of the time-complex matrix, automatically detecting a pattern indicative of one or more of an arrhythmia, a precursor to an arrhythmia, a cardiac event, and/or a precursor to a cardiac event.

BRIEF DESCRIPTION OF THE DRAWINGS

The figures described below depict various aspects of the system and methods disclosed herein. It should be understood that each figure depicts an embodiment of a particular aspect of the disclosed system and methods, and that each of the figures is intended to accord with a possible embodiment thereof. Further, wherever possible, the following description refers to the reference numerals included in the following figures, in which features depicted in multiple figures are designated with consistent reference numerals.

The patent or application file contains at least one drawing executed in color. Copies of this patent or patent application publication with color drawing(s) will be provided by the Office upon request and payment of the necessary fee.

FIGS. 6A-6D illustrate an example matrix formation technique using the localized peak values as performed as part of the process of FIG. 3.

DETAILED DESCRIPTION

Provided are techniques for collecting and analyzing periodic electrical signal data, having period deflection elements, and generating a matrix that depicts those periodic deflection elements in a more compacted manner, making it easier for healthcare professionals to analyze the health condition of a patient based on that data. The electrical signal data may be any cardiac, muscular, or brain activity data, for example. The electrical signal data is characterized by periodic deflection elements that collectively form a periodic signal complex. The periodic signal complex will repeat over the electrical signal data but with different peaks on those deflection elements and different spacings between deflection elements. The present techniques are able to take those different deflection elements and compile them into a multi-dimensional, compacted matrix, that allows for improved pattern recognition in the matrix, as compared to the collected signal data, and that allows for, in some examples, the identification of heretofore un-recognized features in the data. Once formed, the matrices can be used by healthcare professionals to identify physiological conditions in patients, including, in the example of cardiac activity data, arrhythmia conditions and other cardiac conditions.

Figure 1:
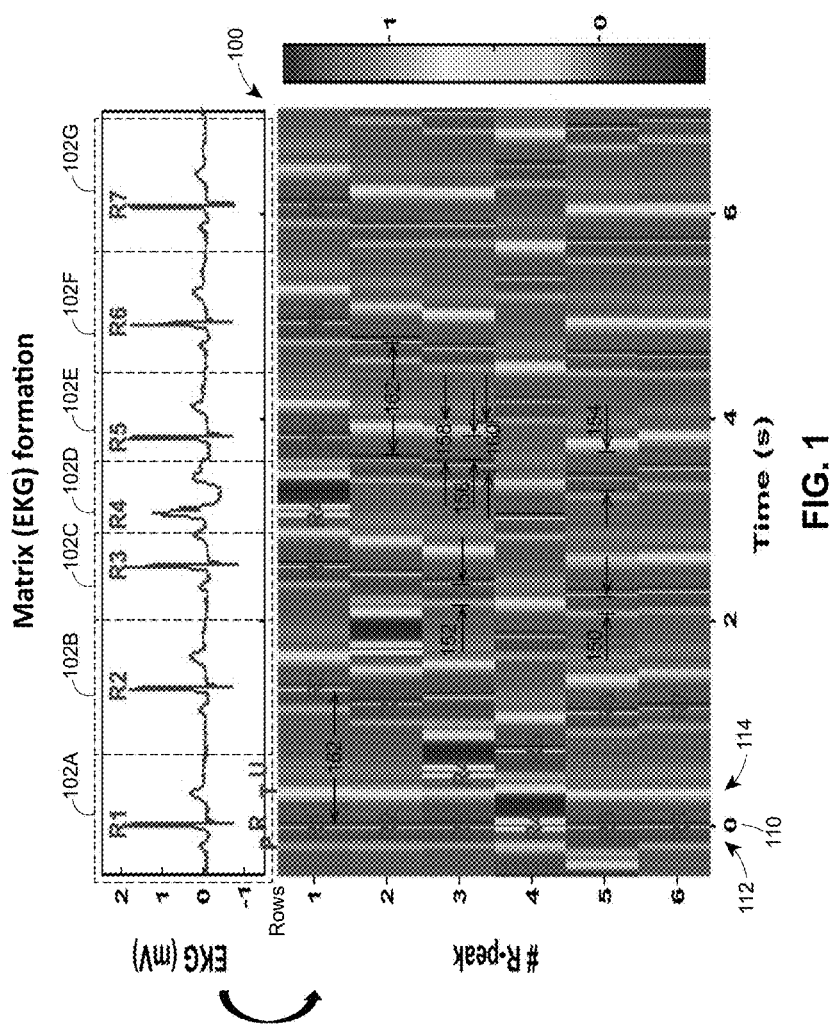
FIG. 1 illustrates an example time-complex matrix formed from electrocardiogram (EKG) signal data.
Figure 2:
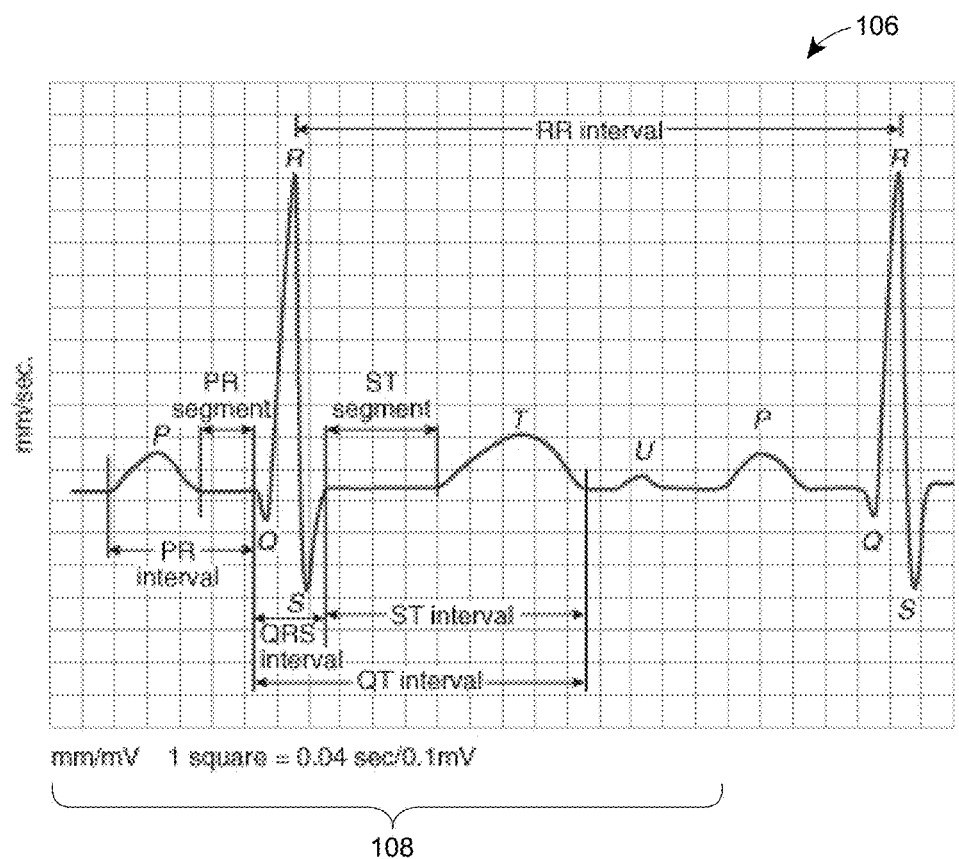
FIG. 2 is an expanded plot of an electrocardiogram electrical signal data showing features within the electrical signal data, features that are displayed over time in the time-complex matric of FIG. 1.

FIG. 1 illustrates a time-complex matrix 100 that has been formed from periodic electrical signal data in the form of electrocardiogram (ECG or EKG) signal data. The terms "ECG" and "EKG" are used interchangeably herein to refer to electrocardiogram information A plot of EKG data 102 comprises a plurality of complexes 102A-102G, each formed of the same deflection elements, but where those deflection elements differ in peak and trough values and spacings. In the illustrated example, the complexes 102A-102G are characterized by peaks in the R value, i.e., with R as the identified local peak deflection element. Values for R1-R7 are shown, respectively. FIG. 2 illustrates an example EKG signal data 106 showing deflection elements that define a complex and various spacing intervals between deflection elements that are all depicted on the matrix 100 and may be analyzed from the matrix 100 for assessing and diagnosing any of a variety of physical conditions for a subject. The signal data 106 includes a P wave, a PR segment, a PR interval, the QRS complex, the QRS interval, an ST segment, ST interval, QT interval, T wave, and U wave, and RR interval, which collectively are referred to herein as a periodic signal complex elements 108 (the RR interval extends between elements. This periodic signal complex 108 repeats over the signal 102, for example, with different values of deflection elements P, Q, R, S, T, and U.

The matrix 100 is termed a complex matrix in that it contains values for the deflection [P, Q, R, S, T, and U] elements included within a periodic signal complex. The values for these deflection elements may be illustrated numerically or in a coded manner, such as color coded or shading coded, as shown. The matrix 100, as explained herein, is able to depict value changes for these deflection elements (P, Q, R, S, T, and U) over time, not only value changes between a single set of deflections elements, e.g., differences between Q trough and R peak, but also changes for each deflection element over time, e.g., differences in P waves over time.

The matrix 100 is an example of a horizontal time progression matrix, with the intensity values on a z-axis, elapsed time on y-axis, the time of the electrical signal elements on the x-axis. It is noted, that the intensity value depictions make the matrix 100 a three dimensional (3D) matrix for the EKG data 102. In other examples discussed herein, matrices are formed as a vertical time progression matrix, still in a 3D presentation.

Whether in a horizontal time progression or a vertical time progression, the matrices described herein, are characterized by a number of features. The matrix 100 includes a zero time level 110. Each instance of the periodic complex 102A-102G, etc. that forms the EKG signal 102 is plotted at this zero time level 110, where each of the periodic complexes 102A-102G, etc. is plotted at this zero time level 110 on a different matrix row. The zero time level 110 serves a centering point for the matrix 100. For each periodic complex 102A-102G, etc. the R wave peak value is plotted at the zero time level 110, such that looking at the column of points on time 0, the matrix 100 displays changes in $R_N$ values over time, N is between 1 and 6 in the illustrated example. For example, R wave peak, $R_1$, from signal complex 102A, has been centered at the zero line 110 in the first row, as indicated. $R_2$, the next R wave peak, has been centered at the zero line 110 in the second row. $R_3$ follows, and so on, with the matrix 100 showing local R wave peaks from $R_1$ to $R_6$ all aligned at level 110.

The value of the local R wave peaks change, as indicated by the changes in intensity on the zero time level 100. The $R_4$ value, for example, has a much lower intensity.

Other characteristics of the matrix 100 include the inclusion of a P wave region 112, to the left of the R peaks aligned at level 110, as the P wave for each periodic complex signal precedes the R wave. The P wave region 112 shows variations in intensity for the local P wave peaks in a similar manner that level 110 shows the variations for the local R wave peaks. Likewise, a T wave region 114 following the R wave region at level 110 is depicted with the matrix 100.

The matrix 100 is characterized by time progression, either by the number of R peaks accumulated as shown (matrix 100) or by elapsed time in seconds, minutes or hours, along the vertical axis. For example, by examining the zero time level 110, from first row at the top to the bottom row, a healthcare professional can determine the intensity changes in the R peak values over that time.

The matrix 100 is also characterized by a time progression along the horizontal axis. Each row shows the periodic signal complex centered at the zero time level 100, one periodic signal complex preceding that centered signal and 6 subsequent periodic signal complexes. Row 1, for example, shows $R_1$ (centered), and $R_2$-$R_7$. Row 2 shows $R_2$ (centered), $R_3$, $R_4$, and so on. By examining across the rows, and as will be discussed further below, a healthcare professional is able to identify patterns and changes in the EKG signal data 102 over time. The matrix 100 can be compacted as desired depending on the amount of EKG signal data collected and analyzed.

Figure 3:
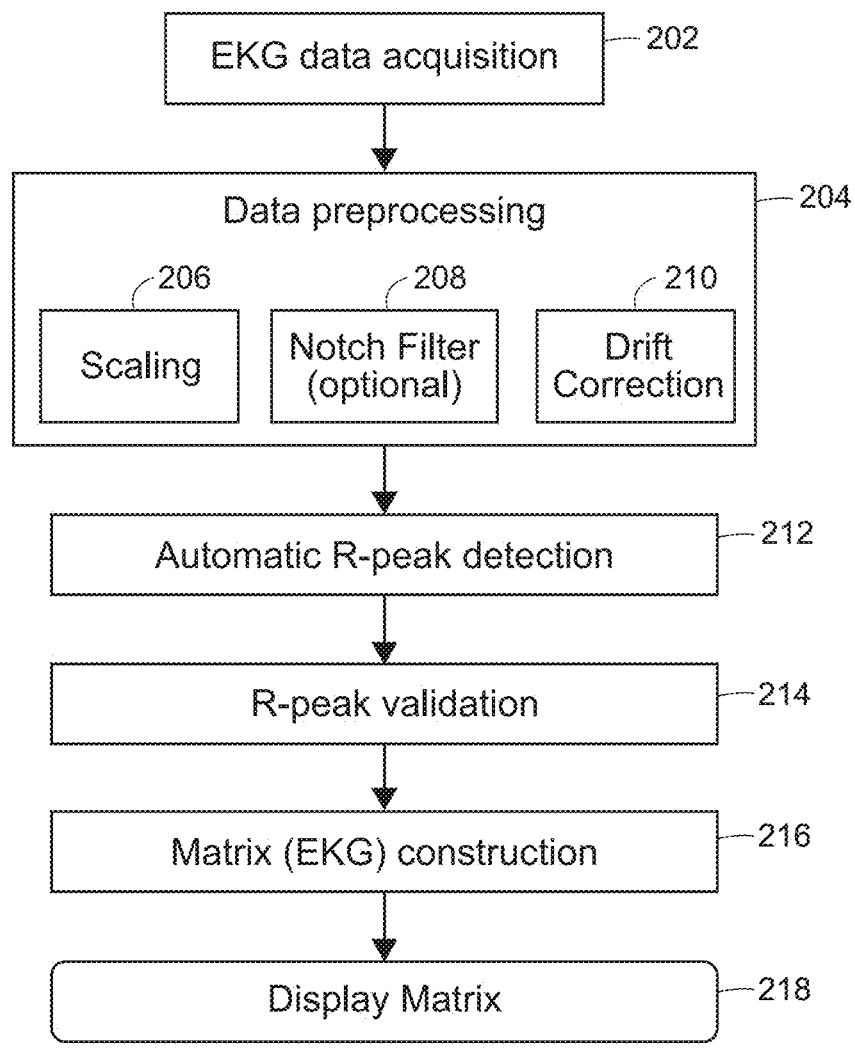
FIG. 3 is a flow diagram of a process for forming the time-complex matrix of FIG. 1.

FIG. 3 illustrates a flow diagram 200 of a process for generating a complex matrix. Initially, EKG data is acquired (block 202), either directly from an EKG machine monitoring a subject or from a database of previously-collected EKG data. That data is collected and provided to a data pre-processing stage (block 204), which may perform scaling on the data (block 206), notch filtering on the data (block 208), and drift correction on the data (210), where each of these may be applied successively on the received data. In other examples, each of the blocks 206-210 is optional.

After pre-processing (block 204), the process 200 performs a localized peak detection, i.e., detection of localized peaks for a deflection within the electrical signal data, using a signal detection module such as module 704 discussed below. For the EKG data signal 102, the peak detection is an R-wave peak ("R-peaks") detection (block 212). The peak detection automatically detects the R-peaks, using a signal detection module, after which the process 200 then optionally validates the detected R-peaks (block 214) to remove spurious peak values and noise in the R-peak detection data. The validation may be automatically performed or performed partially through an interface mechanism. Once the R-peak values have been validated, a time-complex matrix is constructed from the processed EKG signal data (block 216), using a matrix generating module. The process includes coding the data for signal intensity values (for example if shading or coloring coding is to be used), aligning the validated R-peaks at the zero time level 110, and forming the matrix depict the period signal complexes either with a horizontal time progression or with a vertical time progression. An example implementation of the block 216 is shown in FIGS. 6A-6D. After the matrix has been formed, the matrix may be displayed to healthcare professions (218).

Figure 4:
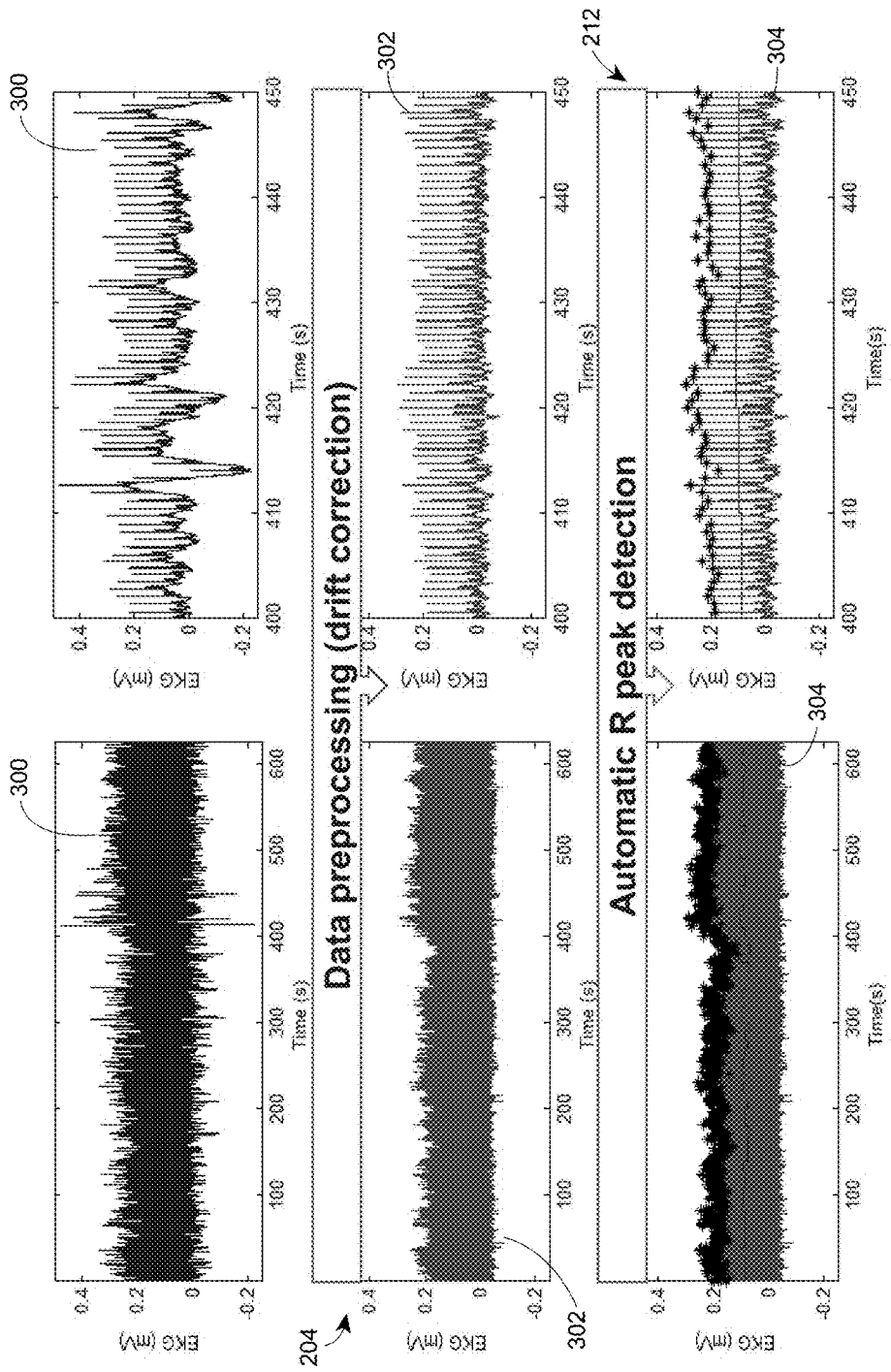
FIG. 4 illustrates an example data processing and local peak detection performed on an electrocardiogram signal as part of the process of FIG. 3.

FIG. 4 illustrates an example of the transformation of EKG signal data that may occur in a first part of process 200. Referring to FIG. 4, EKG data 300 is received at the block 202, and provided to a block 204, which performs baseline drift correction, producing pre-processed data 302, having a baseline that has been normalized, i.e., is 'flatter' in comparison to the received data 300. With the baseline drift correction, the process 200 can then perform more accurate automatic R-peak detection at the block 212, converting the signal data 302 to signal data 304. The transformation from signal data 300 to signal data 302 to signal data 304 is shown over two different time scales for ease of viewing (a longer time window on the left and a shorter time window on the right). The block 212 may determine the local peaks of any deflection element within the EKG periodic signal complex. The R-peak has been chosen for numerous reasons, including the relative size of the R-peak in a normal QRS complex, as well as the importance of RR interval, i.e., the subject's heart rate.

Figure 5:
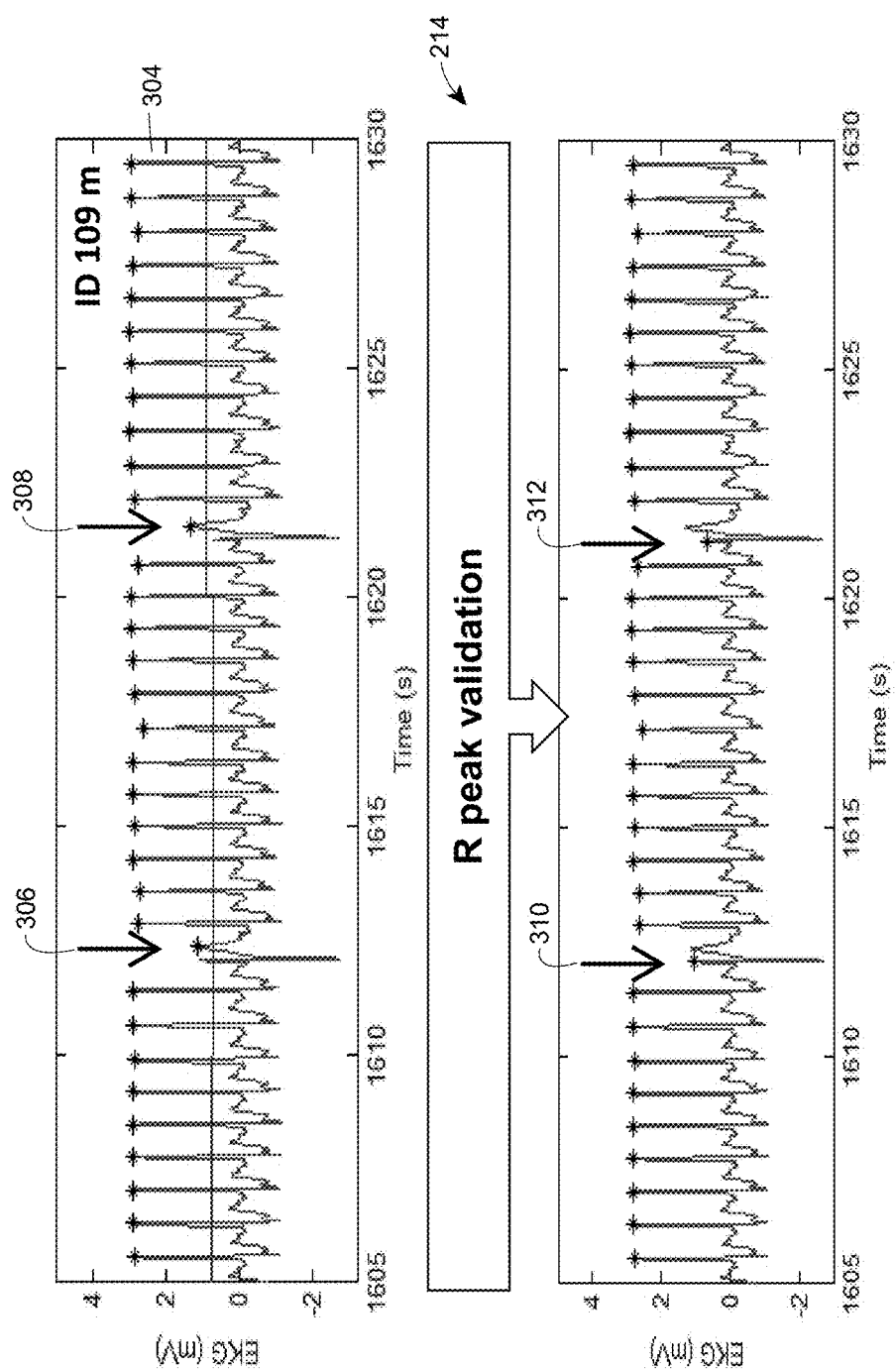
FIG. 5 illustrates an example local peak validation performed on an electrocardiogram electrical signal as part of the process of FIG. 3.

For some EKG signals, the automatic R-peak detection will produce some false R-peaks, in particular where the intensity of the R-wave is at, or near, or below the intensity of T wave. Therefore, in some examples, the optional block 214 is applied to validate the identified R-peaks, an example implementation of which is shown in FIG. 5. The signal data 304, shown over a 25 seconds time window segment, is provided to the block 214, which then determines if identified localized peaks 306 and 308 are indeed R-peaks. The block 214 determines that they are not and identifies new R-peaks 310 and 312, respectively. The block 214 may perform this feature automatically, for example, by identifying R-peaks having a value (measured from a baseline) that is below a threshold value, thereby suggesting a suspect R-peak candidate. The block 214 may then perform additional localized peak and trough detection around the identified R-peak, searching for (in a statistically significant manner) the P-wave peak, Q-wave trough, S trough, and/or T-wave peak. Identifying one or more these and knowing the ordering of the R-wave peak relative to these other deflection elements, the block 214 may then determine that what was previously identified as peaks 306 and 308 were in actuality T-wave peaks following actually R-wave peaks 310 and 312, respectively. Other techniques for R-peak validation will be known.

FIG. 6 illustrates an example time-complex matrix formation as may be performed by the block 216 of process 200. Processed EKG signal data 400 is provided to the block 216, along with an identification of the R-peaks, 1-7, from block 214 as shown (FIG. 6A). The R-peaks from the EKG data 400 are aligned at a zero time level through an alignment process resulting in the alignment matrix 402 (FIG. 6B). The resulting alignment matrix 402 is converted to a time complex matrix 404 through an intensity mapping process. The process 404 converts the intensity values for the deflection elements in the periodic signal complex (P, Q, R, S, T, and U) into relative intensity values using a coded intensity scale 406 (FIG. 6C). For the illustrated example, the matrix 404 (FIG. 6C) is a horizontal time progression matrix, where the time window on the x-axis sets the sampling window, i.e., the number of periodic signal complexes that will be plotted for each R-peak row; whereas the matrix 408 (FIG. 6D is obtained when the matrix 406 is rotated 90 degree counterclockwise. Setting this sampling window to shorter or longer time frames may be determined by healthcare professional depending on the length of the EKG signal, the level of analysis, and the types of analysis they wish to perform on the matrix 408. In any event, the matrix 408 may be formed, by the processes described herein, one row at a time, where each row includes at least two adjacent R peaks (to allow estimation) and the specific periodic signal complexes (identified by their respective $R_N$-peaks), to fit within the sampling window.

Figure 7:
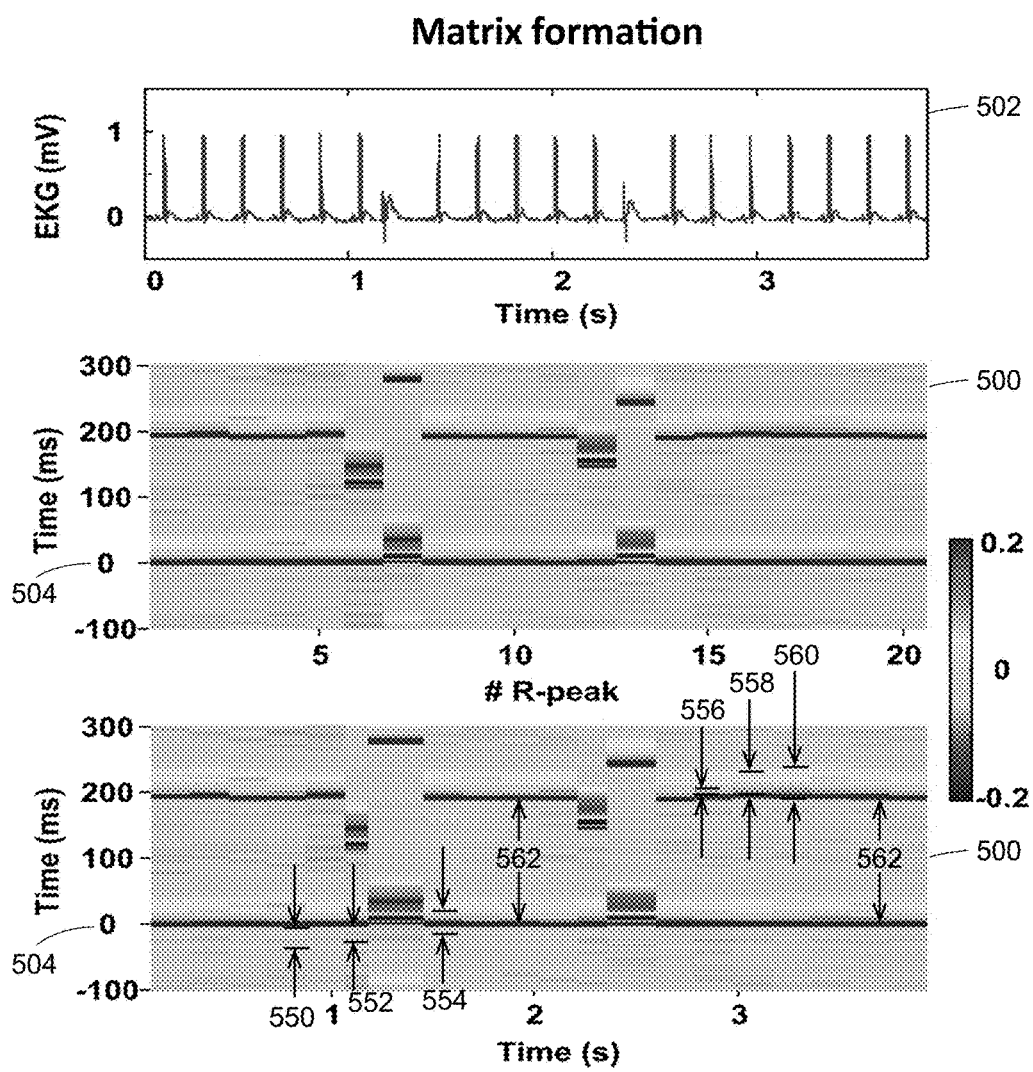
FIG. 7 illustrates another example time-complex matrix formed from electrocardiogram electrical signal data.

FIG. 7 shows another example time-complex matrix 500 that may be formed by the process 200, converting an EKG signal 502. The matrix 500 is similar to matrix 100 of FIG. 1. However, the matrix 500 is formed to have a vertical time progression, in which a zero time level 504 is shown on a y-axis and time values (relative to the center R peaks) extend along this axis. The accumulated R-peak numbers (or length of recorded signal) extend over time along the x-axis, where the automatically identified R-peaks for the signal 502 are each aligned at the zero time level 504, similar to the matrix 100, but along the x-axis. In this orientation, time-dependent changes (along the x-axis) of EKG intervals (e.g., PR intervals, PR segments, QRS intervals, QT intervals, ST segments, ST intervals, and RR intervals, along y-axis), EKG amplitude for various signal peaks (e.g., P, Q, R, S, T, and U peaks, along z-axis), and EKG morphology (e.g., P, Q, R, S, T, and U waves, along both y- and z-axis) are visually apparent. As shown the matrix 500 may be depicted with a R-peak scale on the horizontal axis or a time scale, where the time corresponds to the timing locations of the R-peaks in the EKG signal 502. The illustrated EKG signal data was collected from testing on a rat, in accordance with an example implementation. Human testing was performed as well, and is confirmatory of the illustrated EKG data herein and the analyses thereof.

Figure 8:
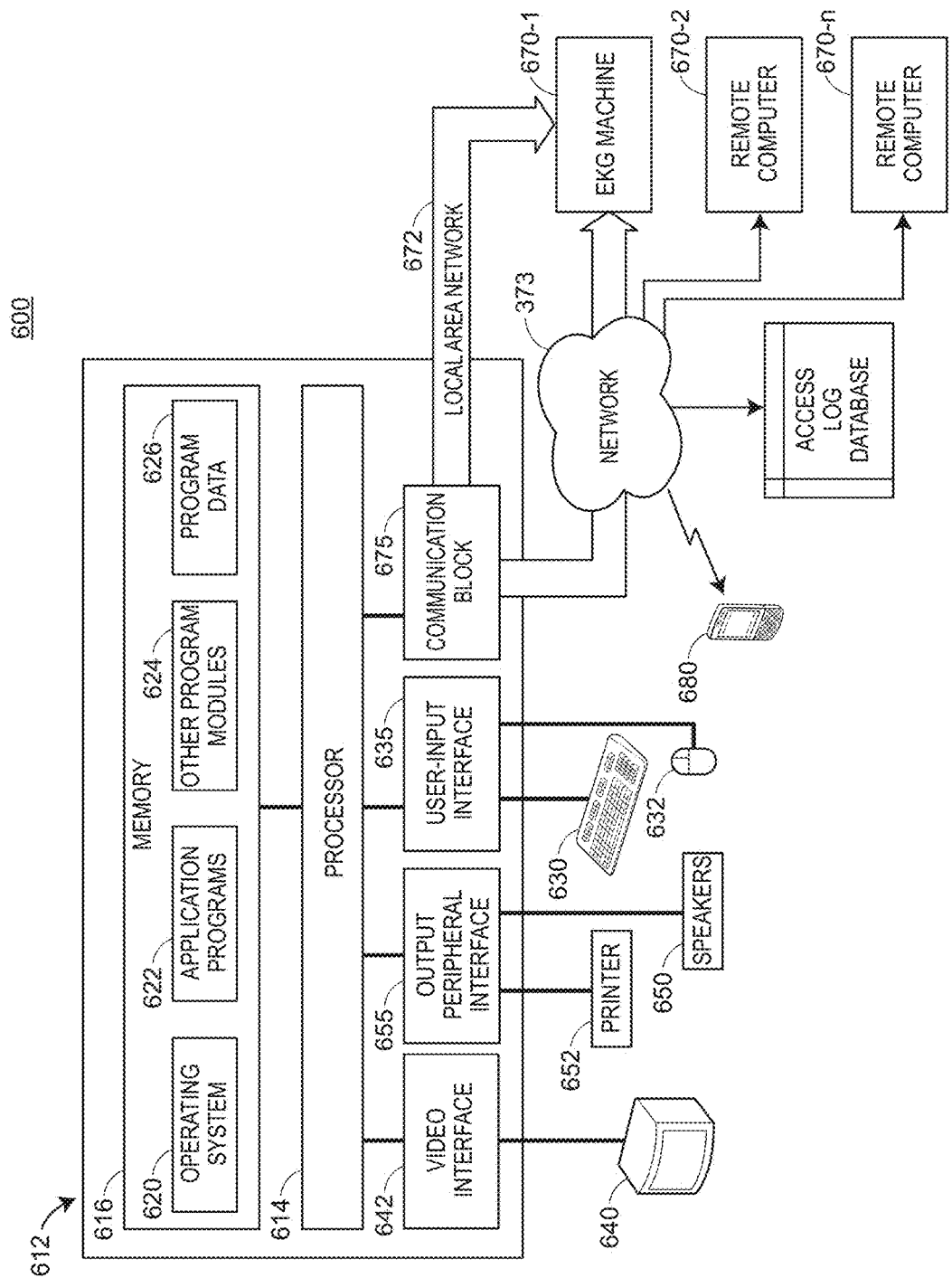
FIG. 8 illustrates a system for analyzing electrocardiogram electrical signal data and forming a time-complex matrix from the signal data.

FIG. 8 illustrates an example computer system that is used to collect periodic electrical signal data of cardiac, muscular, or brain activity, convert that data into a time-complex matrix, and perform analysis on the matrix data. That is, the techniques described above (including the process 200 in FIG. 3) may be coded, in software, hardware, firmware, or combination thereof, for execution on a computing device such as that illustrated in FIG. 8. Generally, FIG. 8 illustrates an example of a suitable computing system environment 600 to interface with a medical professional or other user to analyze medical data, such as electrocardiogram (ECG/EKG), electromyography (EMG) data, and/or electroencephalography (EEG) data, signals captured at the point of assessment or from a stored database of historical signal data. It should be noted that the computing system environment 600 is only one example of a suitable computing environment and is not intended to suggest any limitation as to the scope of use or functionality of the method and apparatus of the claims.

With reference to FIG. 8, the exemplary system 600 for implementing the blocks of the method and apparatus includes a general-purpose computing device in the form of a computer 612. The computer 612 may be a ventricular arrhythmia/VT analysis and mapping system. Components of computer 612 may include, but are not limited to, a processing unit 614 and a system memory 616. The computer 612 may operate in a networked environment using logical connections to one or more remote computers, such as remote computers 670-1, 670-2, . . . 670-n, via a first communication network 672, such as local area network (LAN), and/or a second communication network 673, such as wide area network (WAN) 673, via a communication interface 675. The communication interface 675 may include a variety of hardware for wireless and/or wired communications capabilities. Exemplary wireless communication hardware in the communication interface 675 may include cellular telephony circuitry, GPS receiver circuitry, Bluetooth circuitry, Radio Frequency Identification (RFID) or Near Field Communication (NFC) circuitry, and/or Wi-Fi circuitry (i.e., circuitry complying with an IEEE 802.11 standard), as well as hardware supporting any number of other wireless communications protocols. The communication networks 672 and 673 may be over wireless or wired communication links. Example wired communications may include, for example, USB circuitry, Ethernet circuitry, and/or hardware supporting any number of other wired communications protocols. The network 673 may connect the system 612 to any number of network-enabled devices. The remote computers 670-n may represent a network-enabled wireless terminal, a phone, a tablet computer or personal digital assistant (PDA), a smartphone, a laptop computer, a desktop computer, a tablet computer, hospital terminal or kiosk, a portable media player, an e-reader, or other similar devices (not shown). An example smartphone 680 is shown. Of course, any network-enabled device appropriately configured may interact with the system 600. The computer system 312 may send the matrices to the remote computers 670-n, smartphone 680, or other network-enabled devices for display to healthcare professionals, patients, etc. which devices may display the matrix for interaction by such users.

The remote computers 670 may include other computers like computer 612, but in some examples, these remote computers 670 include one or more of (i) an EKG, EEG, EMG, or other machine that collects electrical signal data indicating cardiac, muscular, or brain activity, (ii) a medical imaging system, and (iii) a signal records database systems, and (iv) a scanner.

In the illustrated example, the computer 612 is connected to a multi-lead EKG apparatus, labeled machine 670-1. The EKG machine 670-1 may be a stand-alone system, having a multi-lead sensor, such as a 612 lead EKG apparatus described above and a processing machine for performing EKG operation, including transmitting stimulation signals, collecting EKG signals at a user selected scan rate, performing signal analysis on collected EKG signals, such as noise filtering, etc., and storing (and/or buffering) those EKG signals and transmitting the same to the computer 612 for further analysis and conversion into the time-complex matrix. In other examples, a multi-lead EKG probe (as described above) may be connected directly to the computer 612, which would then control operation of the multi-lead EKG probe, perform the data processing and storage functions, in place of the remote system 670-1.

Computer 612 typically includes a variety of computer readable media that may be any available media that may be accessed by computer 612 and includes both volatile and nonvolatile media, removable and non-removable media. The system memory 616 includes computer storage media in the form of volatile and/or nonvolatile memory such as read only memory (ROM) and random access memory (RAM). The ROM may include a basic input/output system (BIOS). RAM typically contains data and/or program modules that include operating system 620, application programs 622, other program modules 624, and program data 626. The memory 616 may store instructions that when executed by the processor 614 perform electrical signal pre-processing, local peak detection, validation, and matrix creation in accordance with the examples described here, for example, storing these instructions as the programs 622 and 624 implementing the process 200. The computer 612 may also include other removable/non-removable, volatile/nonvolatile computer storage media such as a hard disk drive, a magnetic disk drive that reads from or writes to a magnetic disk, and an optical disk drive that reads from or writes to an optical disk.

A user may enter commands and information into the computer 612 through input devices such as a keyboard 630 and pointing device 632, commonly referred to as a mouse, trackball or touch pad. Other input devices (not illustrated) may include a microphone, joystick, game pad, satellite dish, scanner, or the like. These and other input devices are often connected to the processing unit 614 through a user input interface 635 that is coupled to a system bus, but may be connected by other interface and bus structures, such as a parallel port, game port or a universal serial bus (USB). A monitor 640 or other type of display device may also be connected to the processor 614 via an interface, such as a video interface 642. In addition to the monitor, computers may also include other peripheral output devices such as speakers 650 and printer 652, which may be connected through an output peripheral interface 655.

Generally, the techniques herein may be coded in any computing language for execution on computer 612. EKG (or other) data may be obtained from the remote computers 670-1, 670-2, . . . 670-n and stored and loaded on to any of the computer storage devices of computer 612. Once the EKG data is obtained, a user may input or select the condition parameters through an input mechanism as described. Although, in other examples, the condition parameters may be pre-selected or automatically determined, for example, based on a particular type of analysis that is to be performed. The output of the executable program (e.g., the matrices) may be displayed on a display (e.g., a monitor 640), sent to a printer 652, stored for later use by the computer 612, or offloaded to another system, such as one of the remote computers 670. The output may be in the form of a time-complex matrix image (such as in FIGS. 10A-10P and 11A-11M), a graph, a table or any combination thereof, by way of example. Operations of the system may be recorded in a log database 677 for future reference as shown. This log database may be accessed at subsequent times.

Returning to FIG. 1, the matrix 100 readily displays features of the periodic signal complex, such as, PR segment, the PR interval, the QRS complex, the QRS interval, the ST segment, ST interval, QT interval, as well as features across complexes, such as RR interval (heart rate), as well as trends in these such features over time. For example, the matrix 100 depicts a PR interval 150, a PR segment 152, a QRS interval 154, a ST segment 156, an ST interval 158, a QT interval 160, and an RR interval 162, for various different periodic signal complexes. While only a few such features are labeled, it will be appreciated that patterns in such features will be apparent over time, whether looking at immediately adjust periodic signal complexes (on the same row) or looking at longer term trends on the vertical axis. The matrix 500 is shown with the same features but oriented for horizontal time progression [(accumulative R peak #s (top panel) or length of recorded signals (bottom panel)]: a PR interval 550, a PR segment 552, a QRS interval 554, a ST segment 556, an ST interval 558, a QT interval 560, and an RR interval 562.

Figure 9:
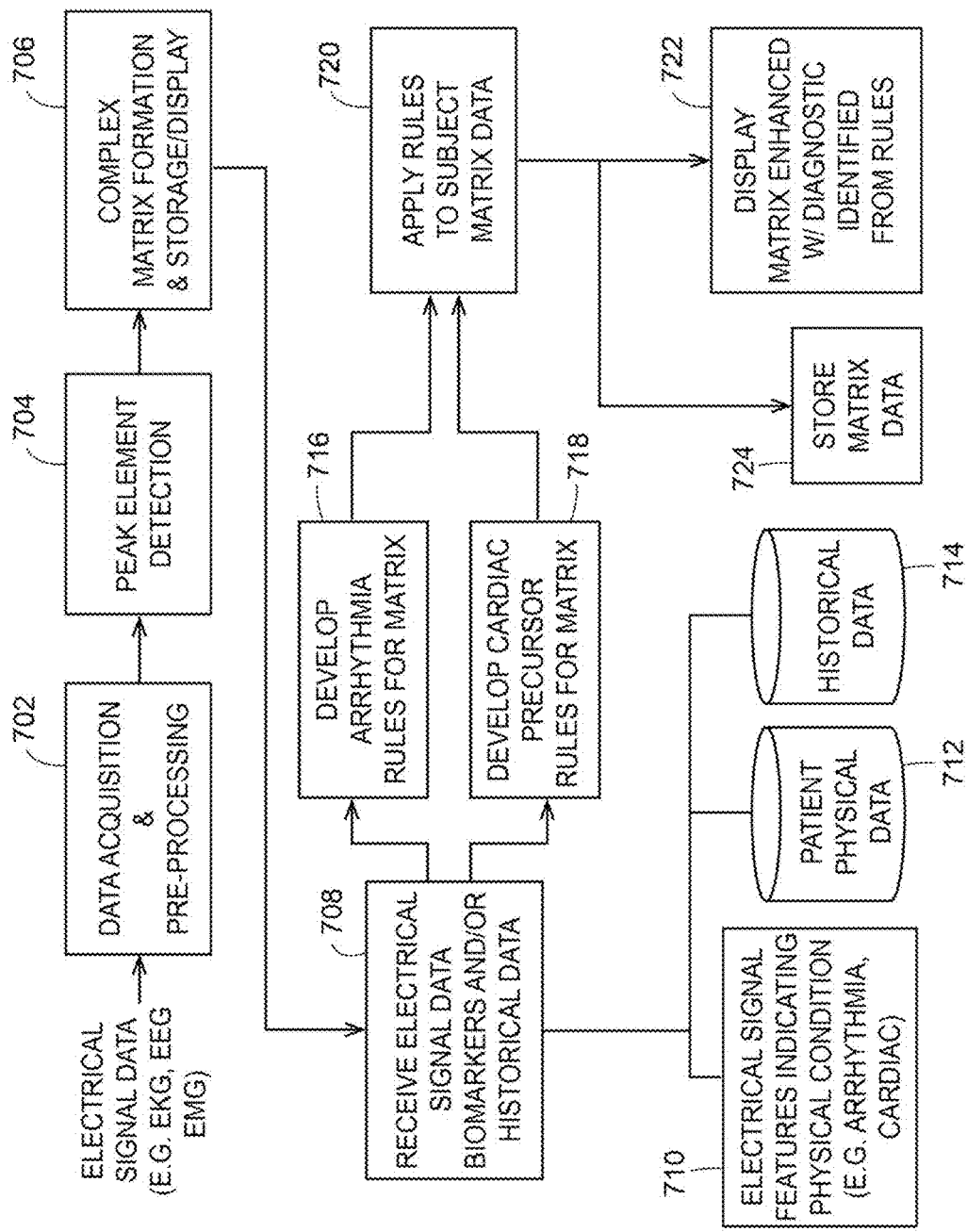
FIG. 9 illustrates an example system for analyzing time-complex matrices to identify indicators of physiologic conditions in the matrix data.

In addition to forming a time-complex matrix, the techniques herein may be used to automatically analyze the time-complex matrix, search for patterns in the matrix by applying patterns rules. These rules include rules for diagnosing arrhythmia conditions and precursors to cardiac conditions, precursors being events that precede physiological events of interest. FIG. 9 illustrates a matrix analysis system 700 that may be implemented on the computer system 600 and used for automatically generating a time-complex matrix from electrical signal data and automatically analyzing that data, using developed rules, for displaying indicators of physiological conditions on the time-complex matrix. In particular, electrical signal data (e.g., EKG/ECG, EEG, or EMG) with a periodic signal complex, is received at a data acquisition and pre-processing module 702, which may perform functions as described in reference to the process 200, for example. Peak element detection module 704 receives the electrical signal data and supplies it to a matrix generating module 706 that generates the time-complex matrix, for example, the horizontal time progression or vertical time progression matrix.

Once formed the system 700 provides the matrix to an analysis stage, which may also be implemented through executable code stored on the computer 612. Initially, the matrix is supplied to electrical signal data collection module 708. The module 708 collects data indicative of features that healthcare professionals use to identify various arrhythmia and cardiac conditions. For example, the system 700 may be used to automatically analyze a time-complex matrix for patterns indicative of any one of atrial premature contraction (APC), aberrated APC, blocked APC, supraventricular tachycardia, atrial flutter, atrial fibrillation, junctional tachycardia, premature ventricular contraction (PVC), interpolated PVC, ventricular bigeminy, ventricular trigeminy, ventricular couplets, ventricular tachycardia, 2nd degree (Mobitz I and Mobitz II) heart block, 3rd degree (or complete) heart block, heart block followed by atrial tachycardia (AT), and heart blockage. Each of these conditions can be detected from the matrix by looking at one or more of periodic deflection elements, P elements, Q elements, R elements, S elements, and T elements, RR interval changes, left bundle branch blockage, right bundle branch blockage, ST depression, ST elevation, QT interval changes, QRS interval changes, PR interval changes, split P-waves, and widened QRS bases indicative of Wolff-Parkinson-White heart beats. Correlations between these elements and the corresponding arrhythmia and cardiac conditions will be known. By way of example, healthcare professionals generally associate flat heart rate turbulence following a PVC event with an increased risk for sudden death. The features data are stored in a database 710, in the illustrated example. That database may store, in a table format, different physiological conditions and different elements that can indicate the physiological condition, and different values for each of the indicating elements (values such as a range of time for an interval, a peak intensity value for an element, an element intensity value below a threshold, an element intensity value above a threshold, spacing distance between elements, a spacing distance between elements of different periodic signal complexes, average intensity values over a sampling window, a range of intensity values over a sampling window, etc.).

In some examples, current patient data (other than the electrical signal data) from a database 712 is provided to the module 208, data such as physiologic condition data (such as body temperature, blood pressure, respiratory rate) and physical characteristic data (such as age, weight, sex, ethnic background, family history of inherited diseases). Historical electrical signal data from a database 714 may also be collected by the module 708.

The data from module 708 is provided to two different rules development modules 716 and 718 that convert the data into rules compatible with application onto a matrix dataset. In the illustrated example, the module 716 produces a set of arrhythmia search rules and the module 718 produces a set of cardiac precursor rules, some examples of which are described further below, in reference to FIGS. 10A-10P and FIGS. 11A-11M.

An analysis module 720 applies the received rules to the receive matrix, from module 706, and produces searches for patterns corresponding to those rules. Any identified patterns are then provided to a display module 722 for display and a storage module 724 for storage. Examples of the display of matrices enhanced to identify pattern data are provided in FIGS. 10A-10P and FIGS. 11A-11N.

Figure 10A:
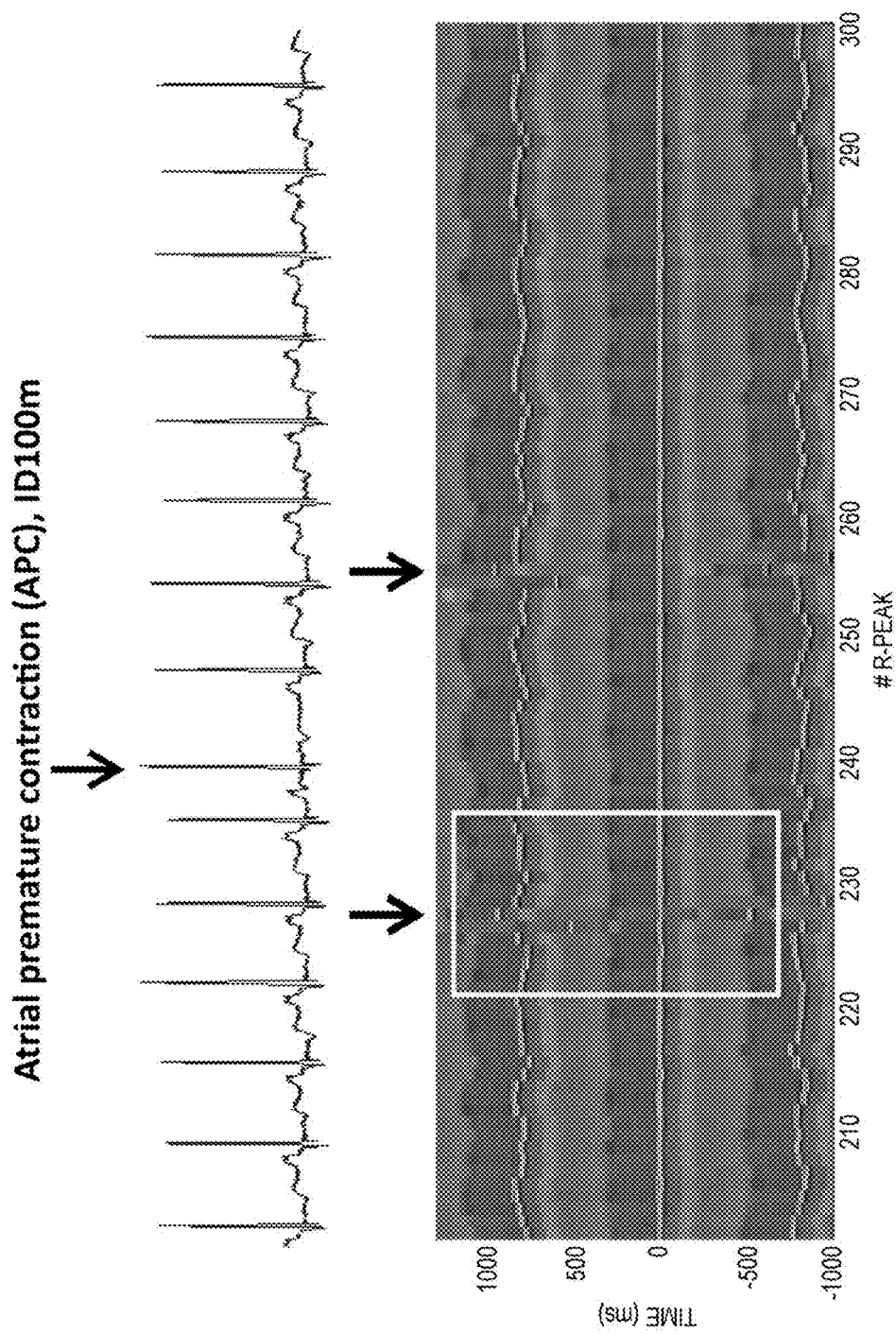
FIGS. 10A-10P illustrate time-complex matrices depicting different arrhythmia conditions detectable in matrix data, with the figures showing a long term matrix display and EKG data corresponding to a highlighted portion of the matrix.
Figure 10C:
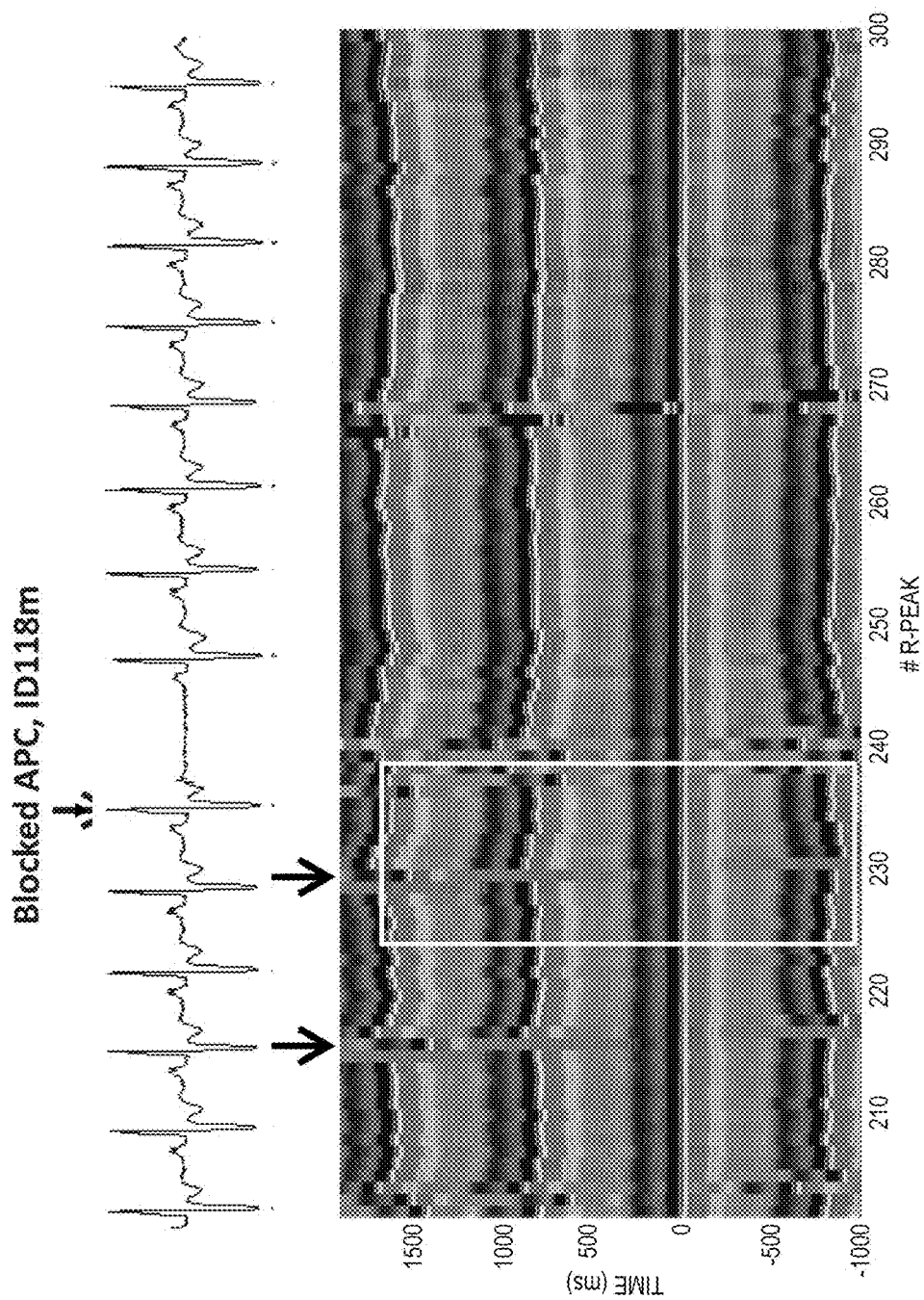
Figure 10D:
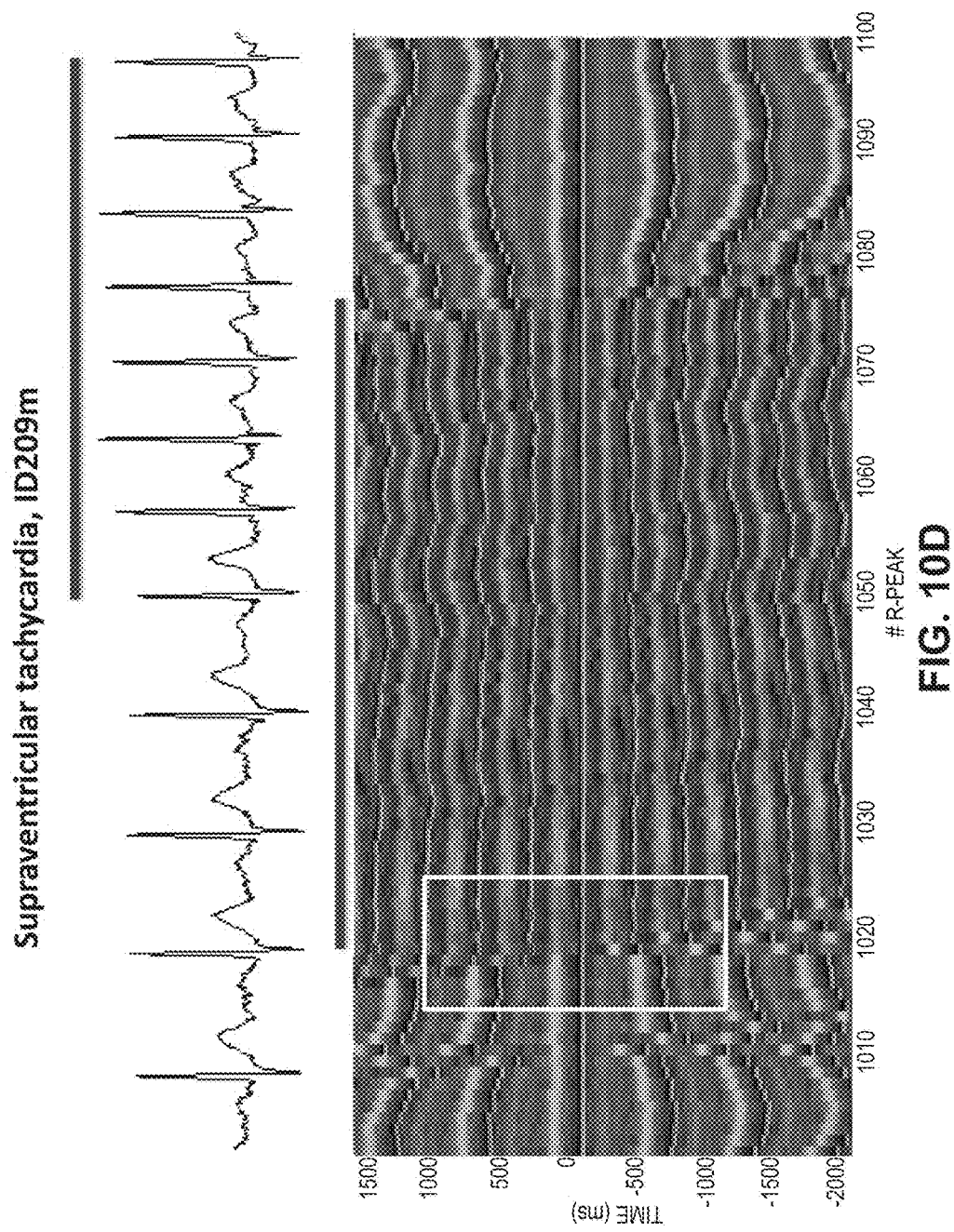
Figure 10E:
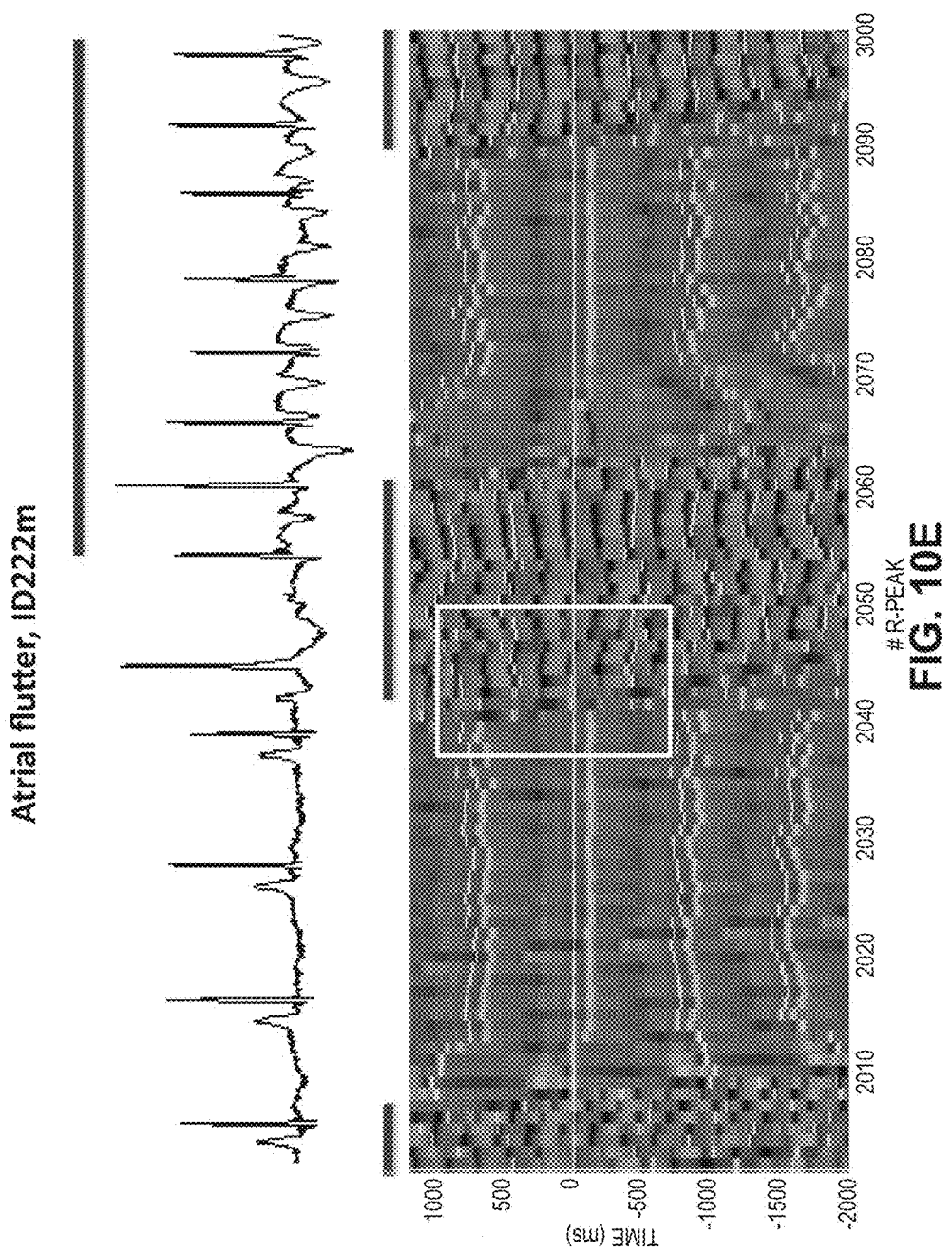
Figure 10F:
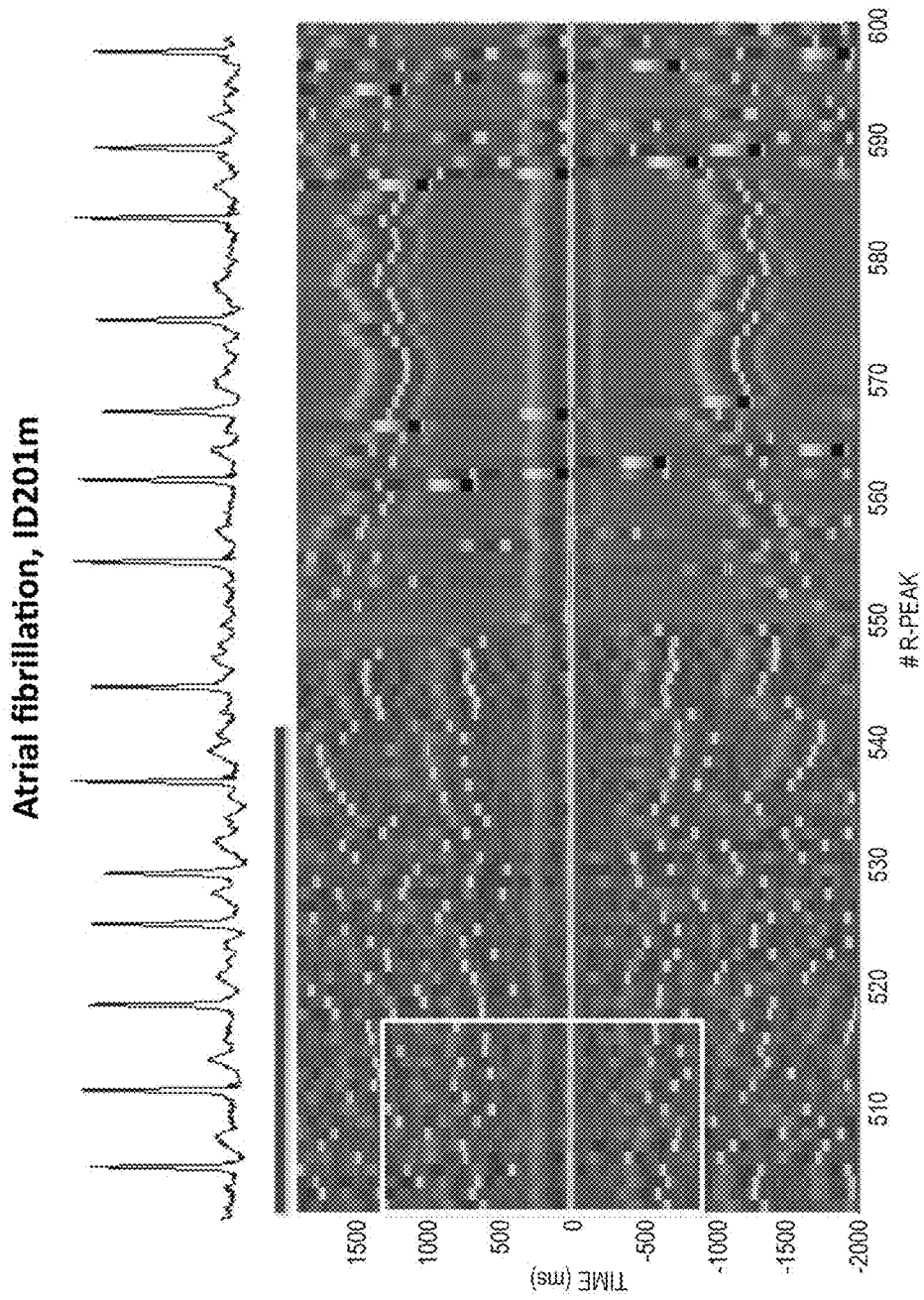
Figure 10G:
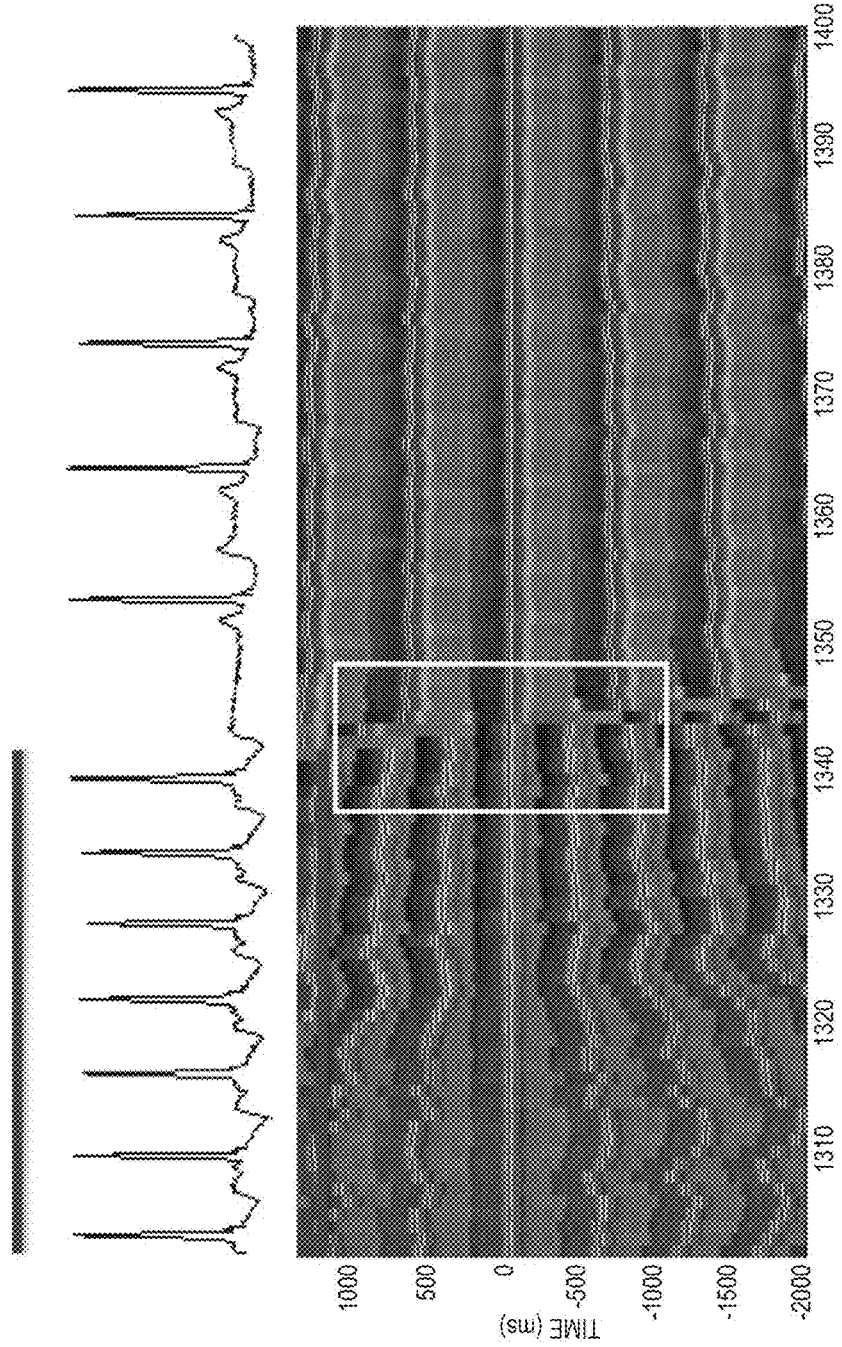
Figure 10H:
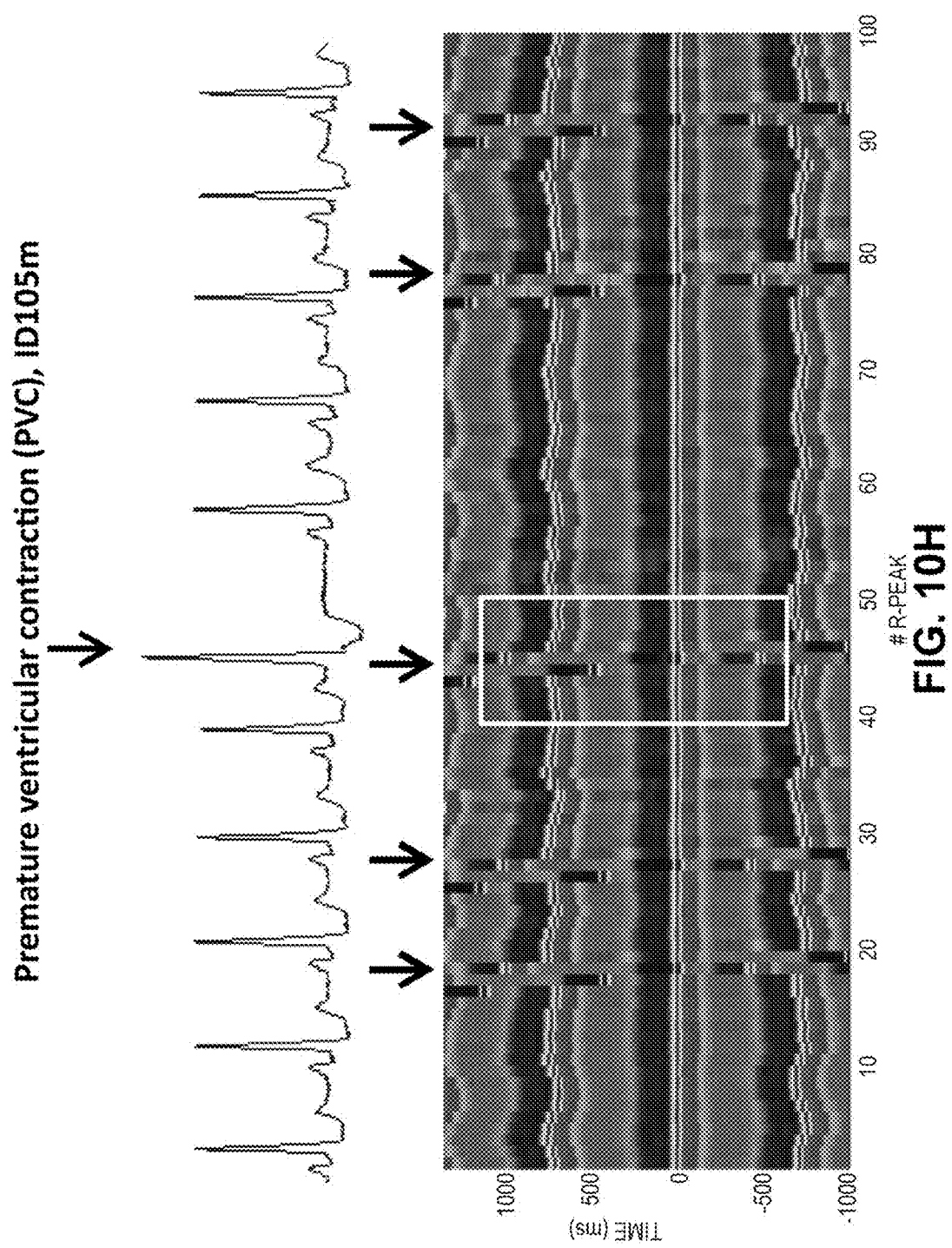
Figure 10I:
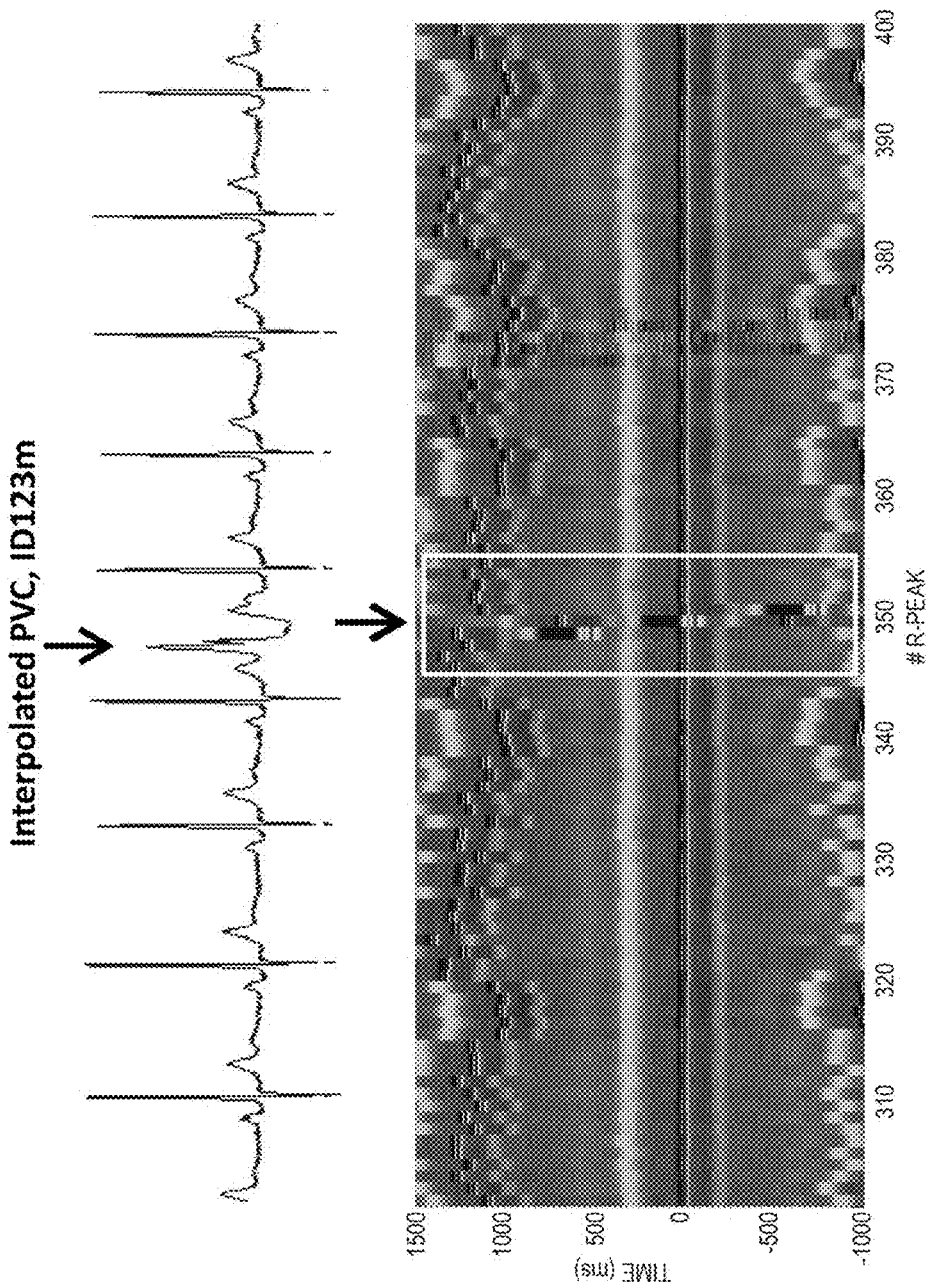
Figure 10J:
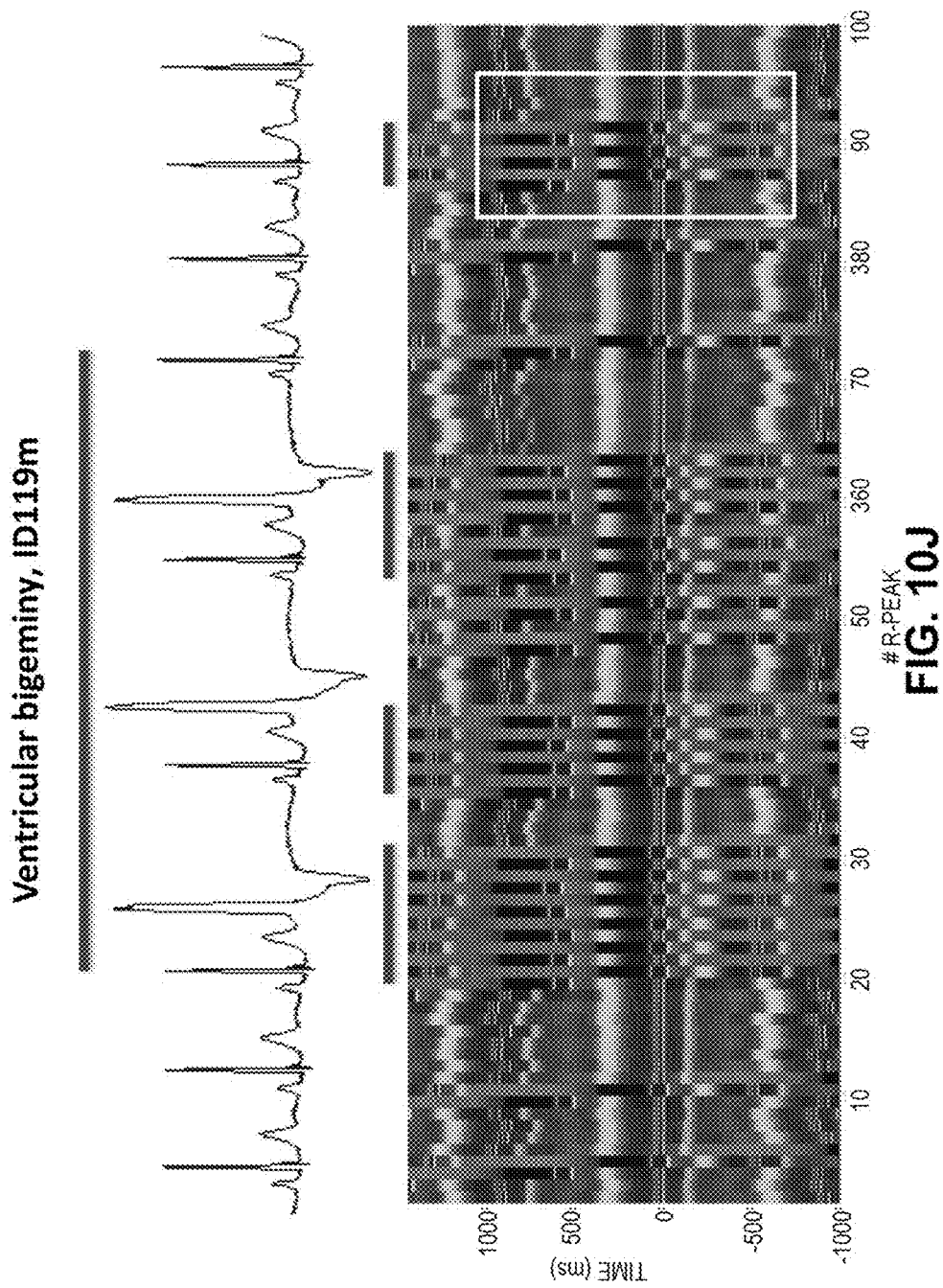
Figure 10K:
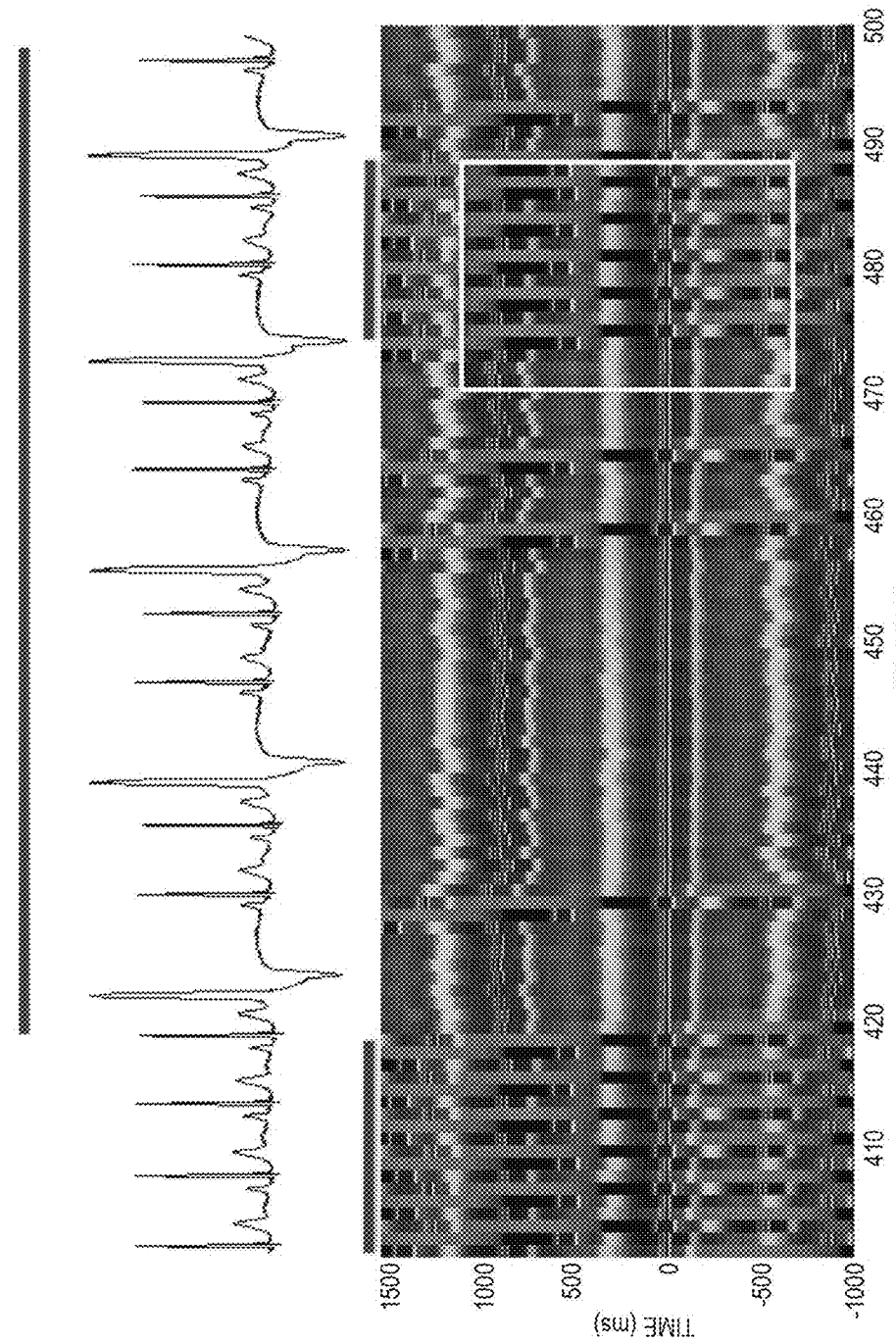
Figure 10L:
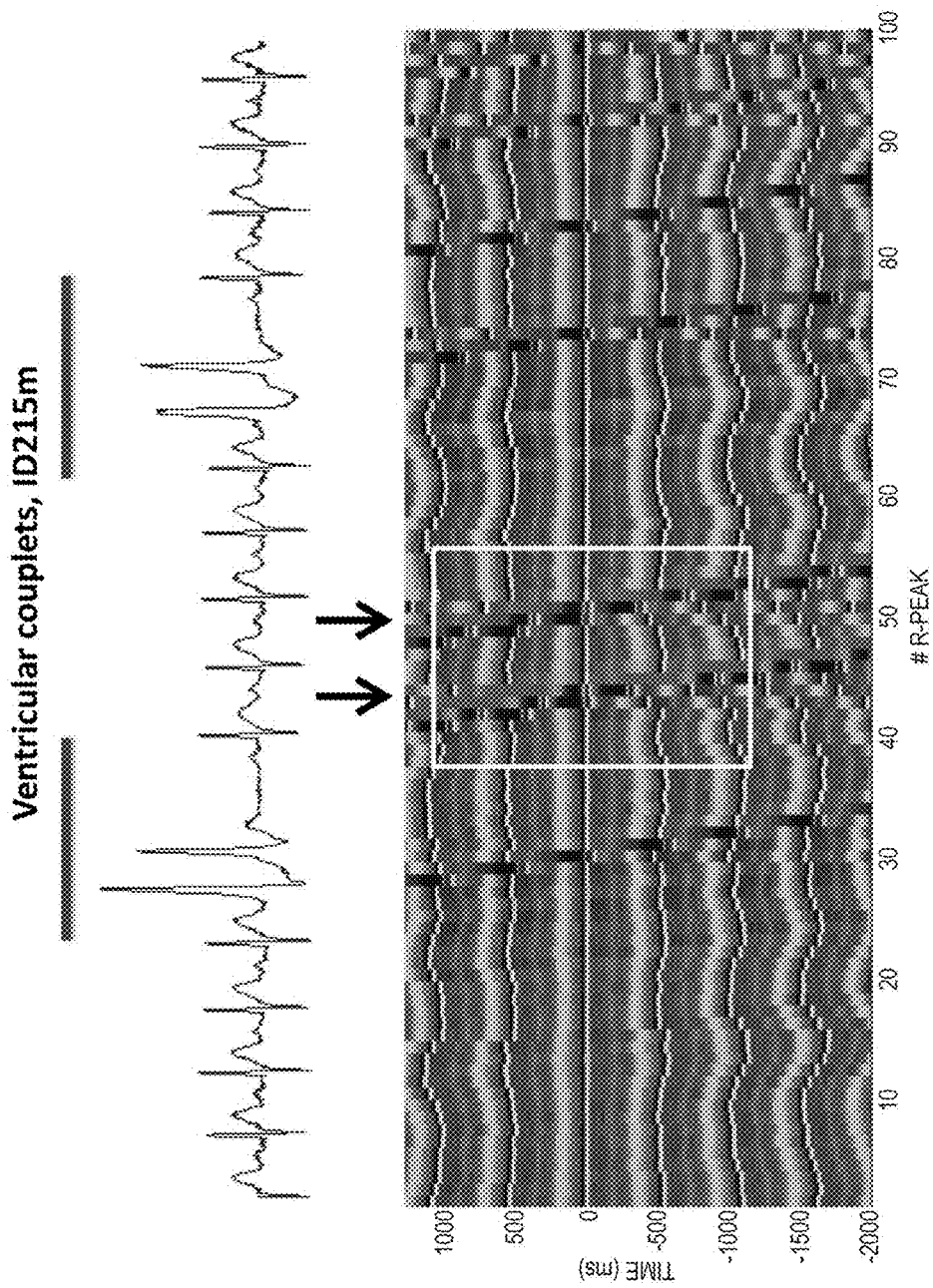
Figure 10M:
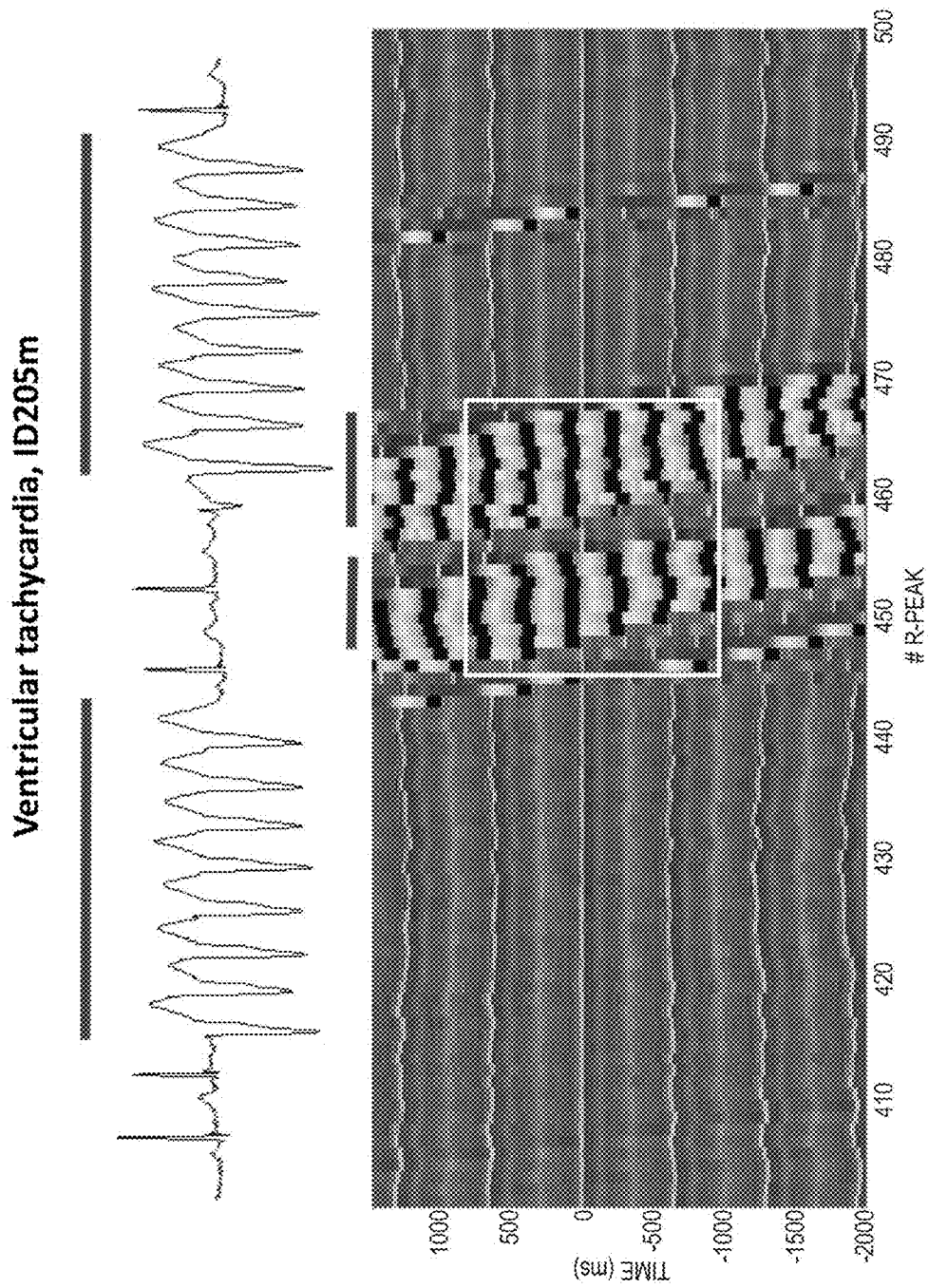
Figure 10N:
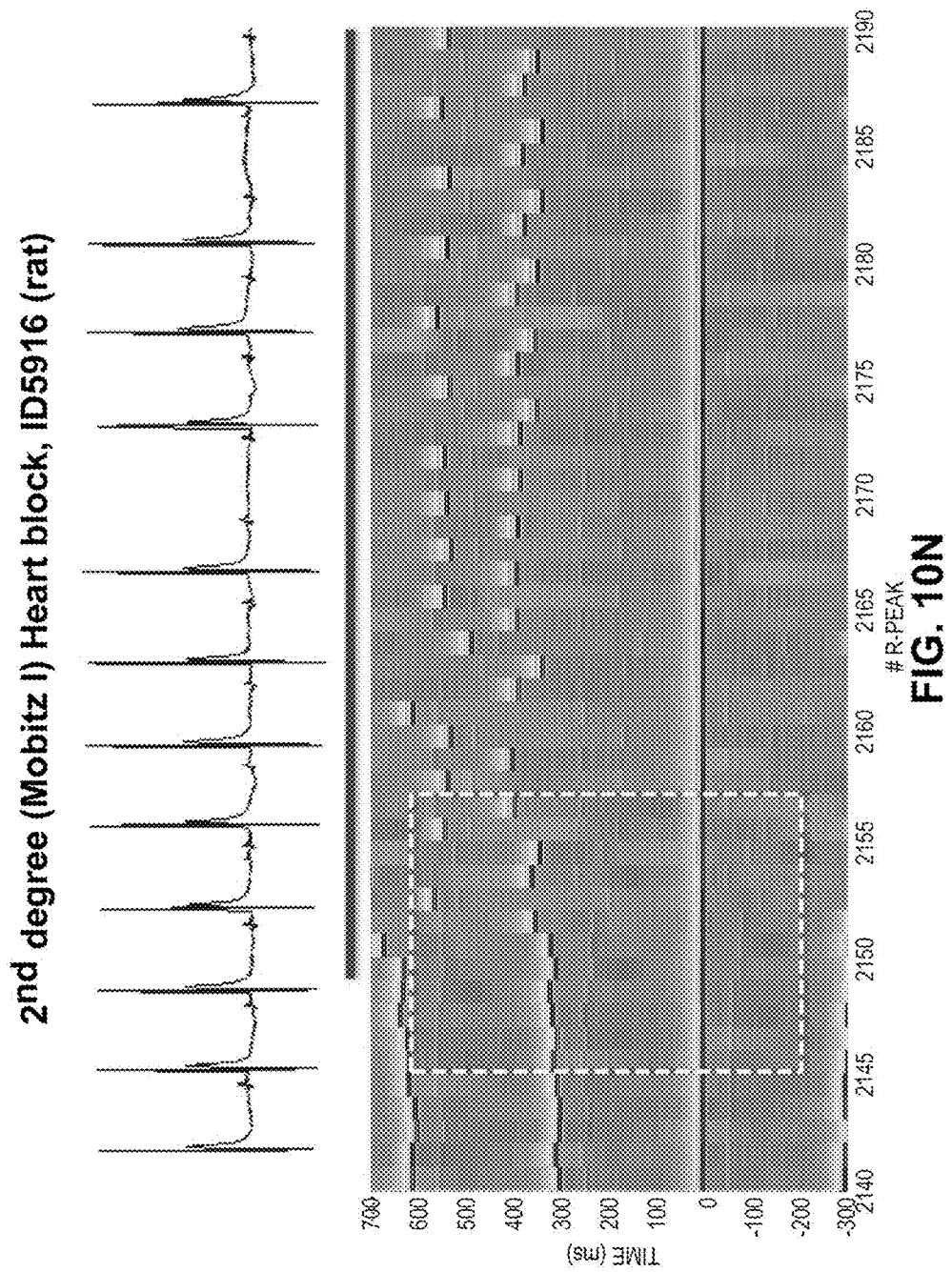
Figure 10O:
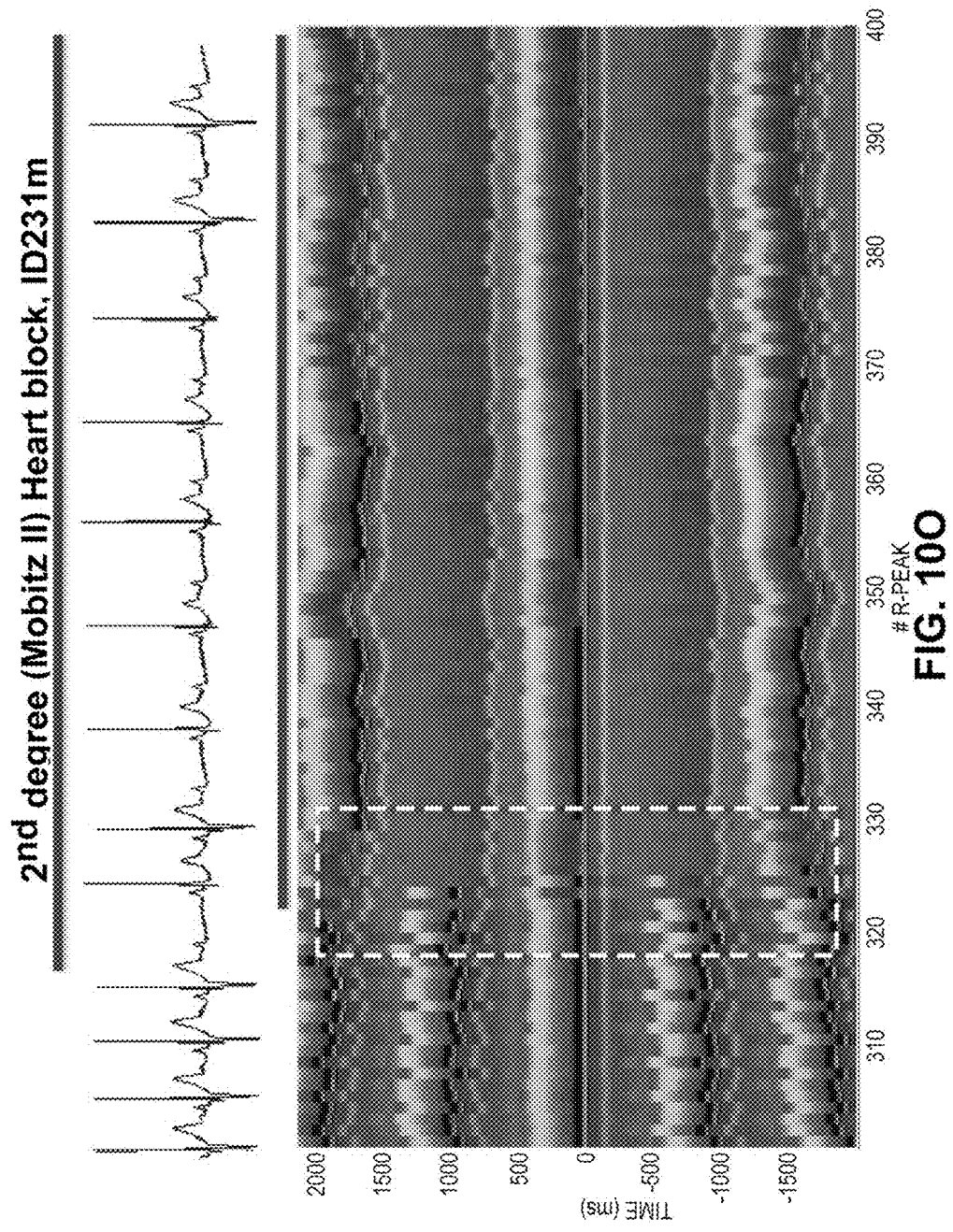
Figure 10P:
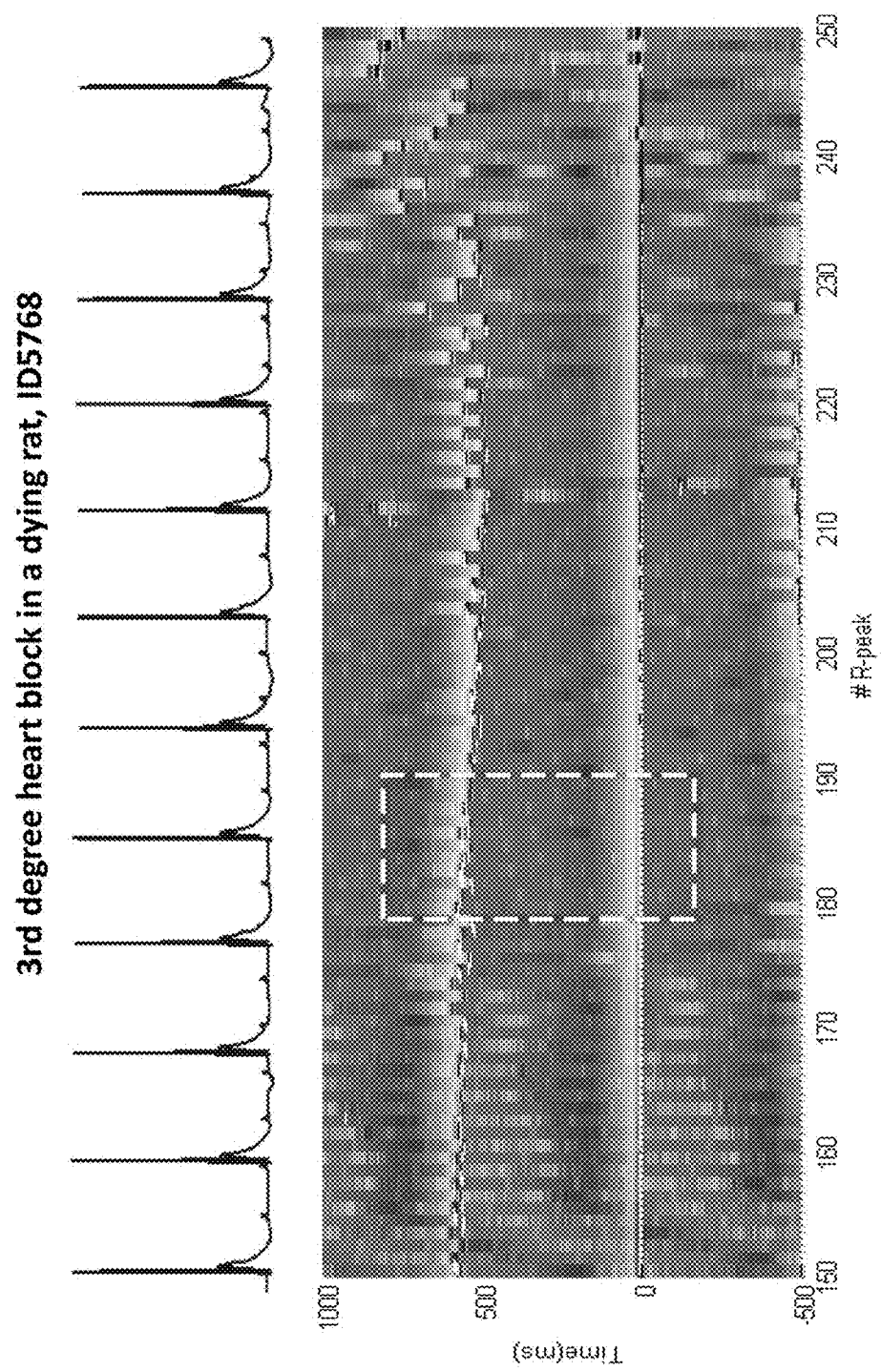

FIGS. 10A-10P illustrate different automatically identified patterns for atrial premature contraction (APC or PAC; common cardiac dysrhythmia that can occasionally trigger atrial flutter or atrial fibrillation), aberrated APC (can indicate heart disease or an increased risk for other cardiac arrhythmia), blocked APC (occurs when the premature beat is very early and the AV node is refractory and the beat is not followed by a QRS complex) this is associated with similar risk as the APC beats), supraventricular tachycardia (rapid heart rhythm originating at or above the AV node; can be perceived as pounding heart with shortness of breath and chest pain or dizziness), atrial flutter (a form of supraventricular tachycardia that often found in individuals with hypertension, coronary artery disease, and cardiomyopathy), atrial fibrillation (abnormal and fast heart rhythm associated with palpitations, fainting, chest pain, or congestive heart failure; associated with increased risk for stroke), junctional tachycardia (a form of supraventricular tachycardia associated with the generation of impulses in the region of AV node; associated with conduction system disease), premature ventricular contraction (PVC; occurs when the heartbeat is initiated by Purkinje fibers; may be perceived as a skipped beat; associated with increased risk of all cause mortality and cardiac death), interpolated PVC (an early ventricular beat sandwiched between two normal beats), ventricular bigeminy (premature ventricular beat occur in every other beat, sandwiched between two sinus beats), ventricular trigeminy (every third beat is premature ventricular beat), ventricle couplets (paired abnormal ventricular beats), ventricular tachycardia (rapid heart beat that starts in the ventricles, potentially life-threatening arrhythmia), $2^{nd}$ degree (Mobitz I) heart block (progressive prolongation of the PR interval on consecutive beats followed by a blocked P wave, is usually benign), $2^{nd}$ degree (Mobitz II) heart block (intermittently non-conducted P waves not preceded by PR prolongation and not followed by PR shortening with fixed number of non-conducted P waves for every successfully conducted QRS complex), and $3^{rd}$ degree heart block (or complete heart block, which occurs when impulse generated in the SA node does not propagate to the ventricles; associated with coronary ischemia or myocardial infarction), respectively.

Figure 11A:
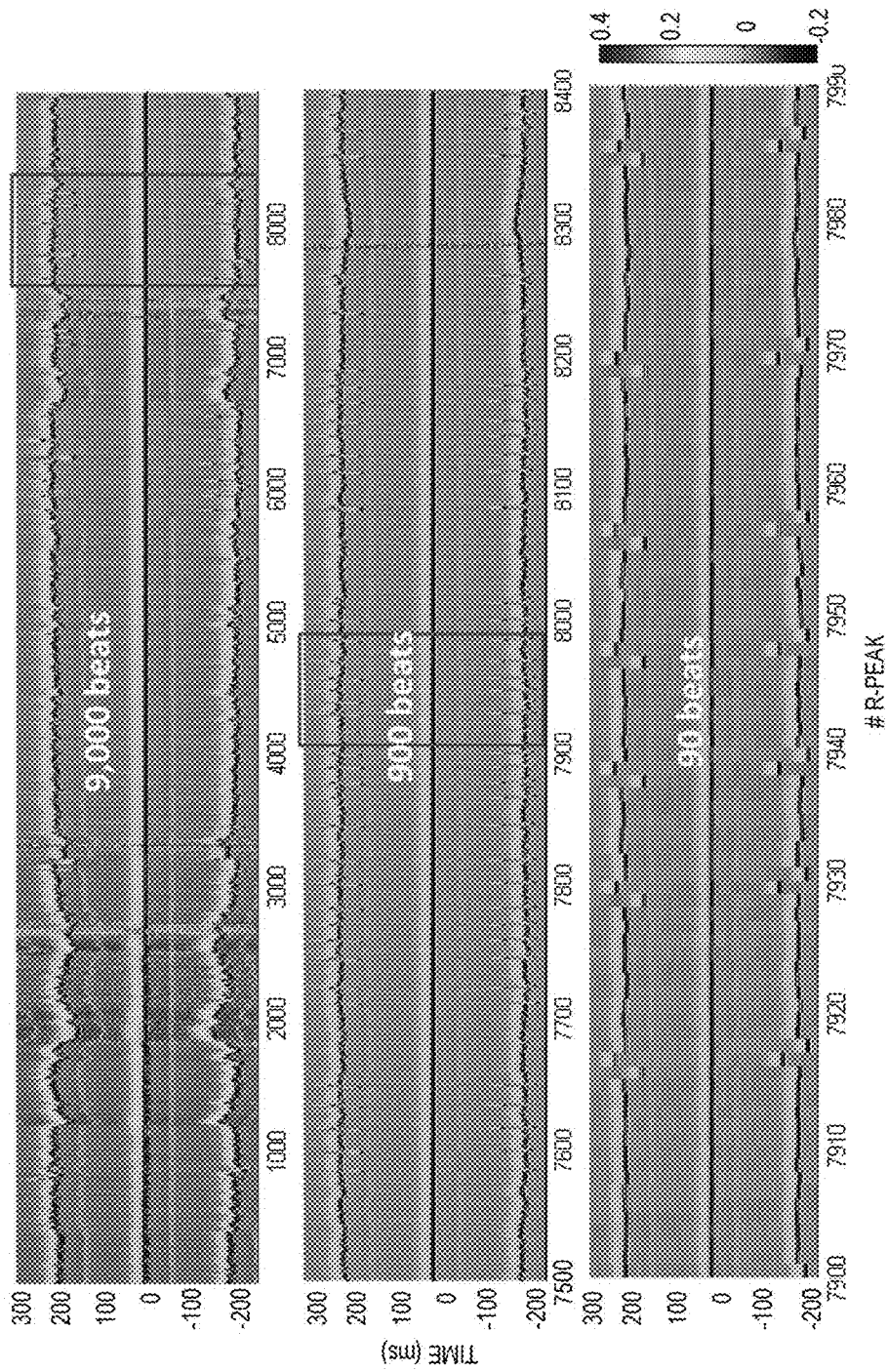
FIGS. 11A-11N illustrate time-complex matrices depicting different cardiac conditions detectable in matrix data, with the figures showing a long term matrix display and EKG data corresponding to a highlighted portion of the matrix.
Figure 11B:
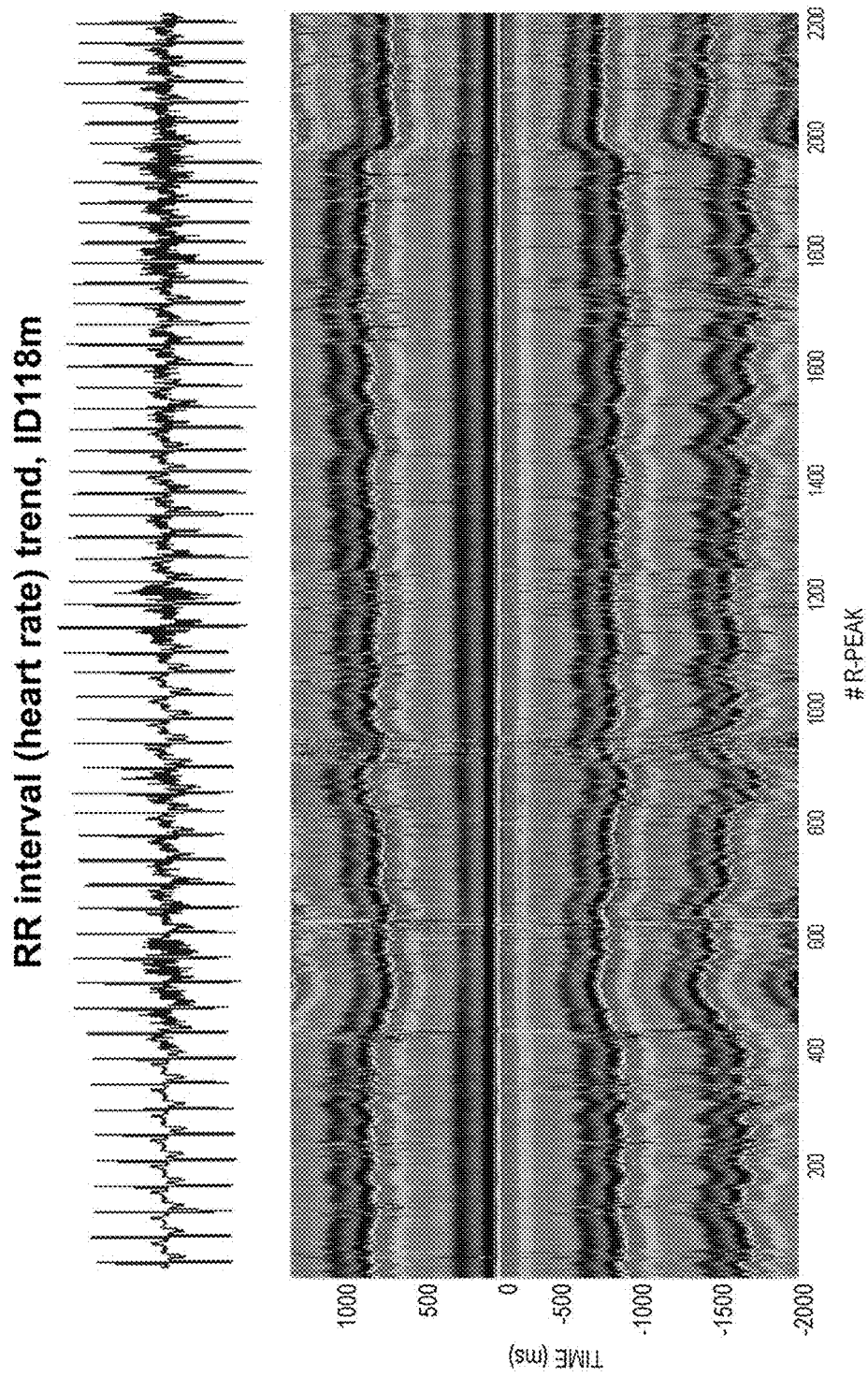
Figure 11C:
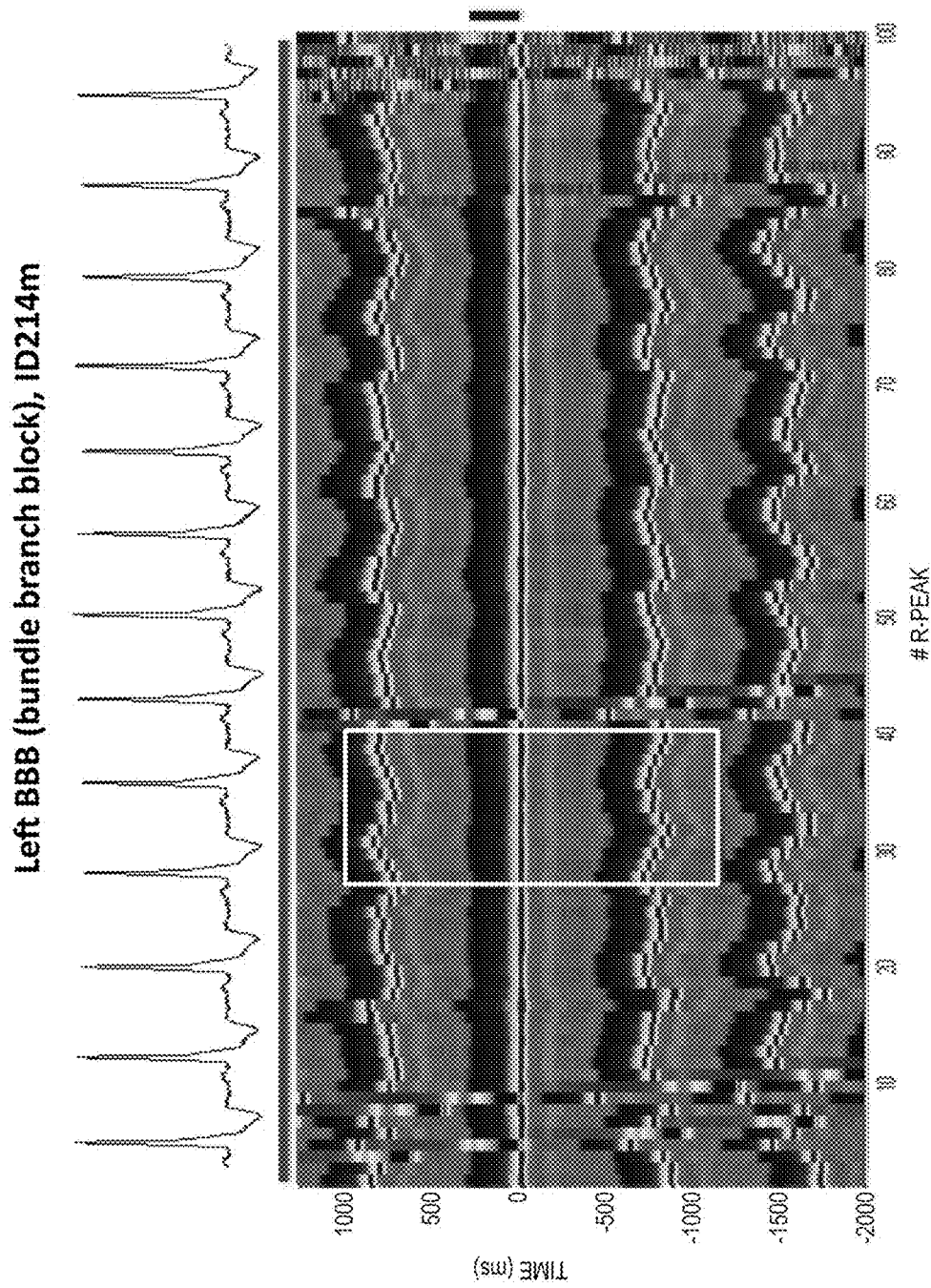
Figure 11D:
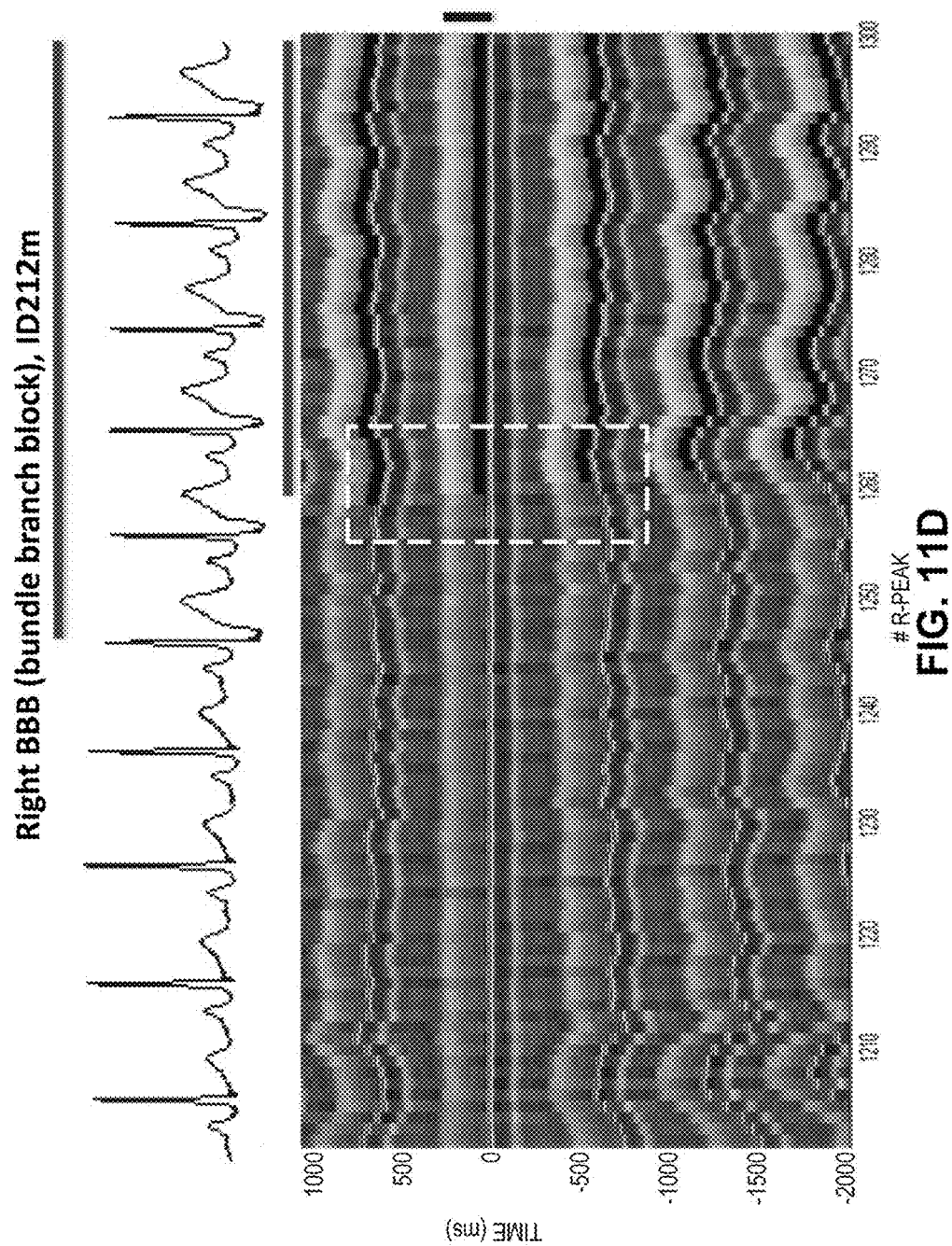
Figure 11E:
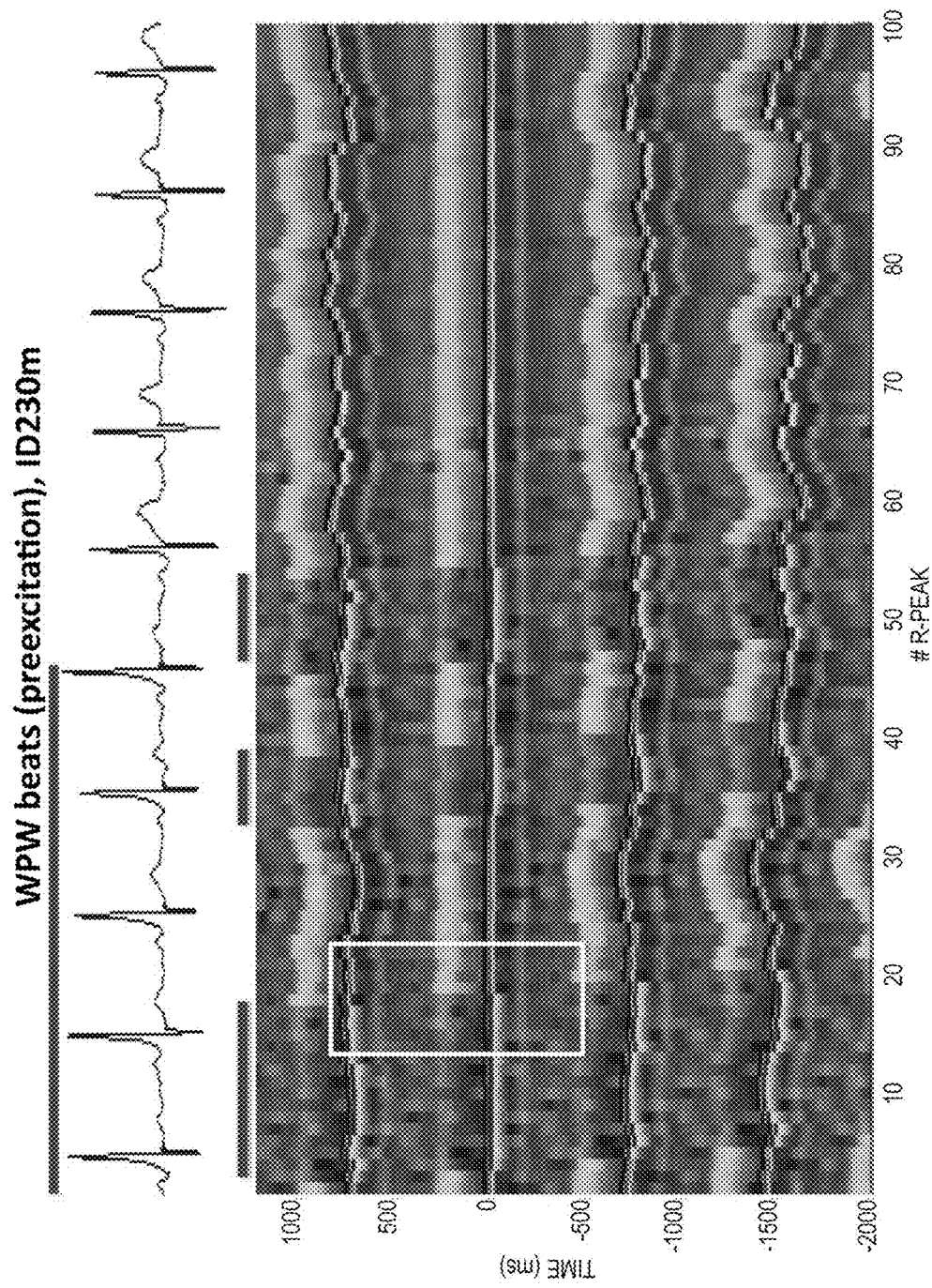
Figure 11F:
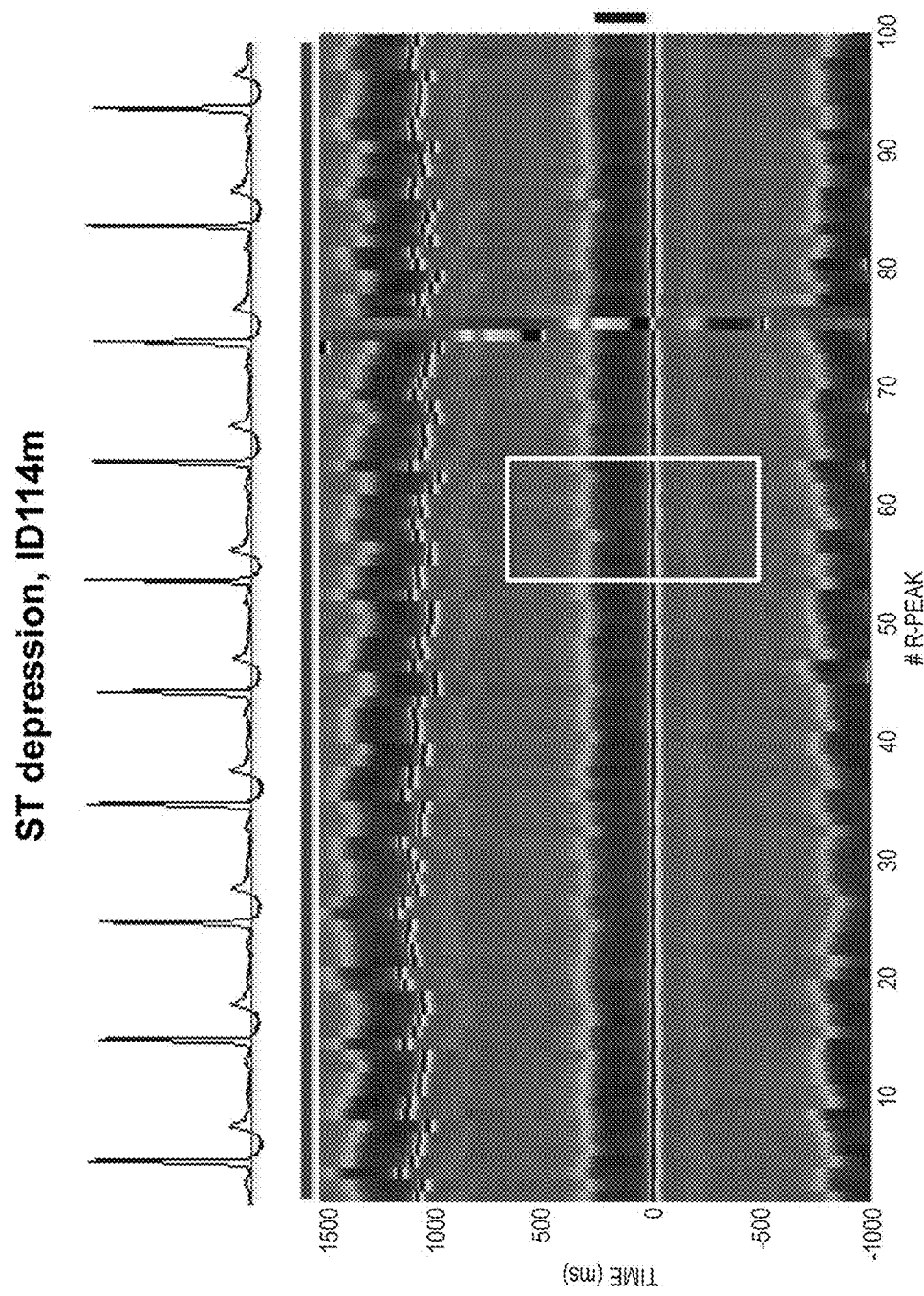
Figure 11G:
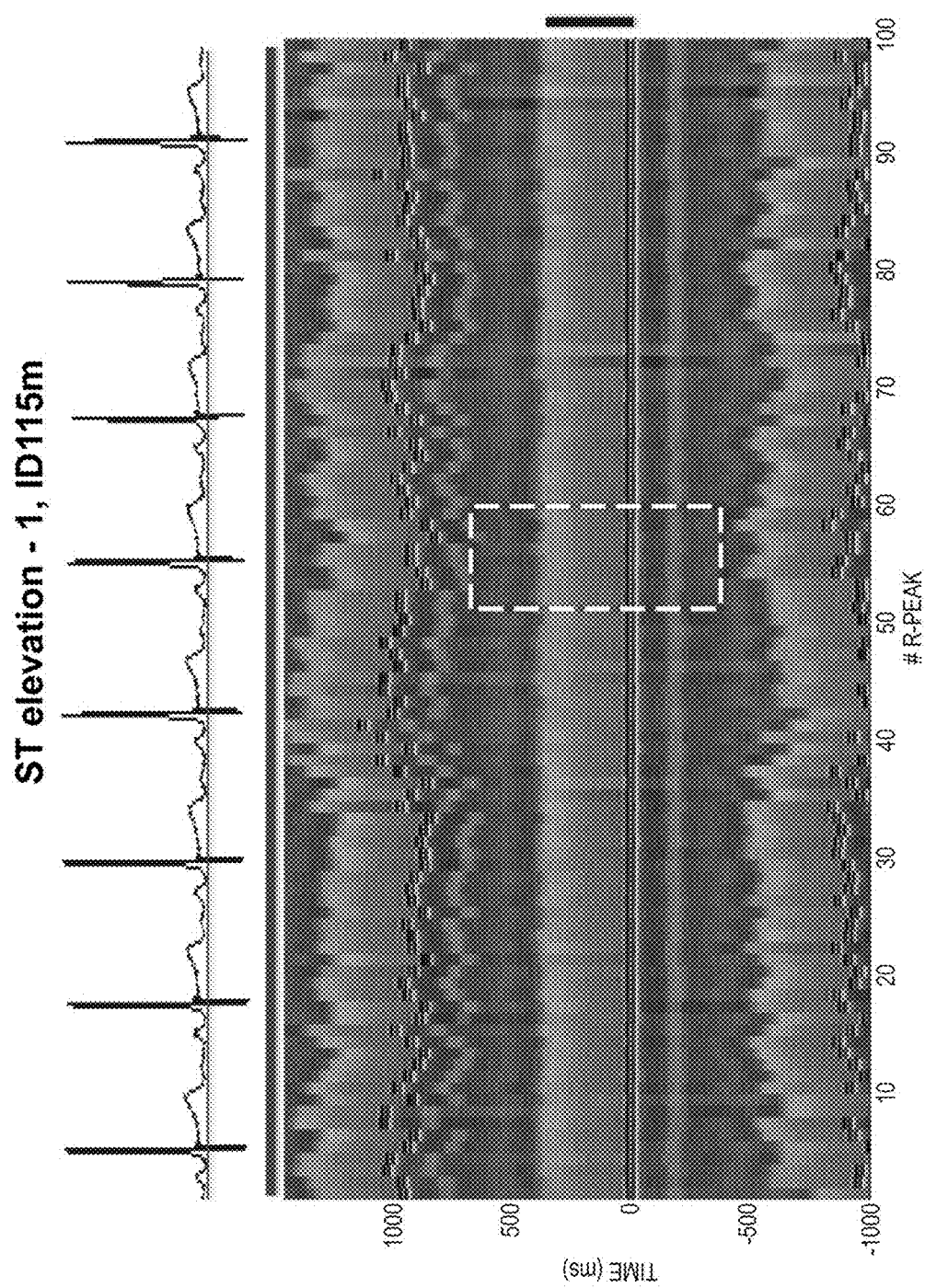
Figure 11H:
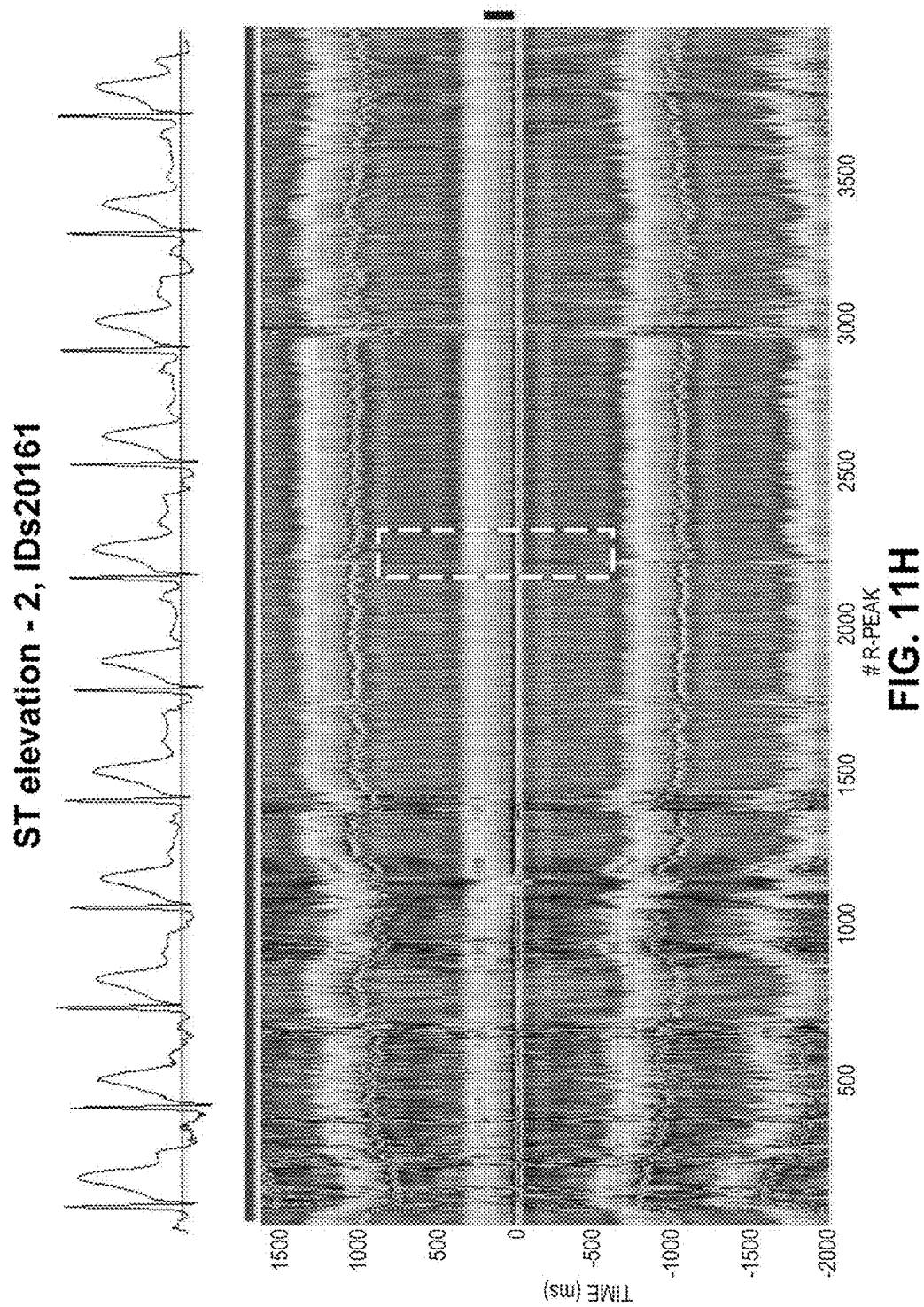
Figure 11I:
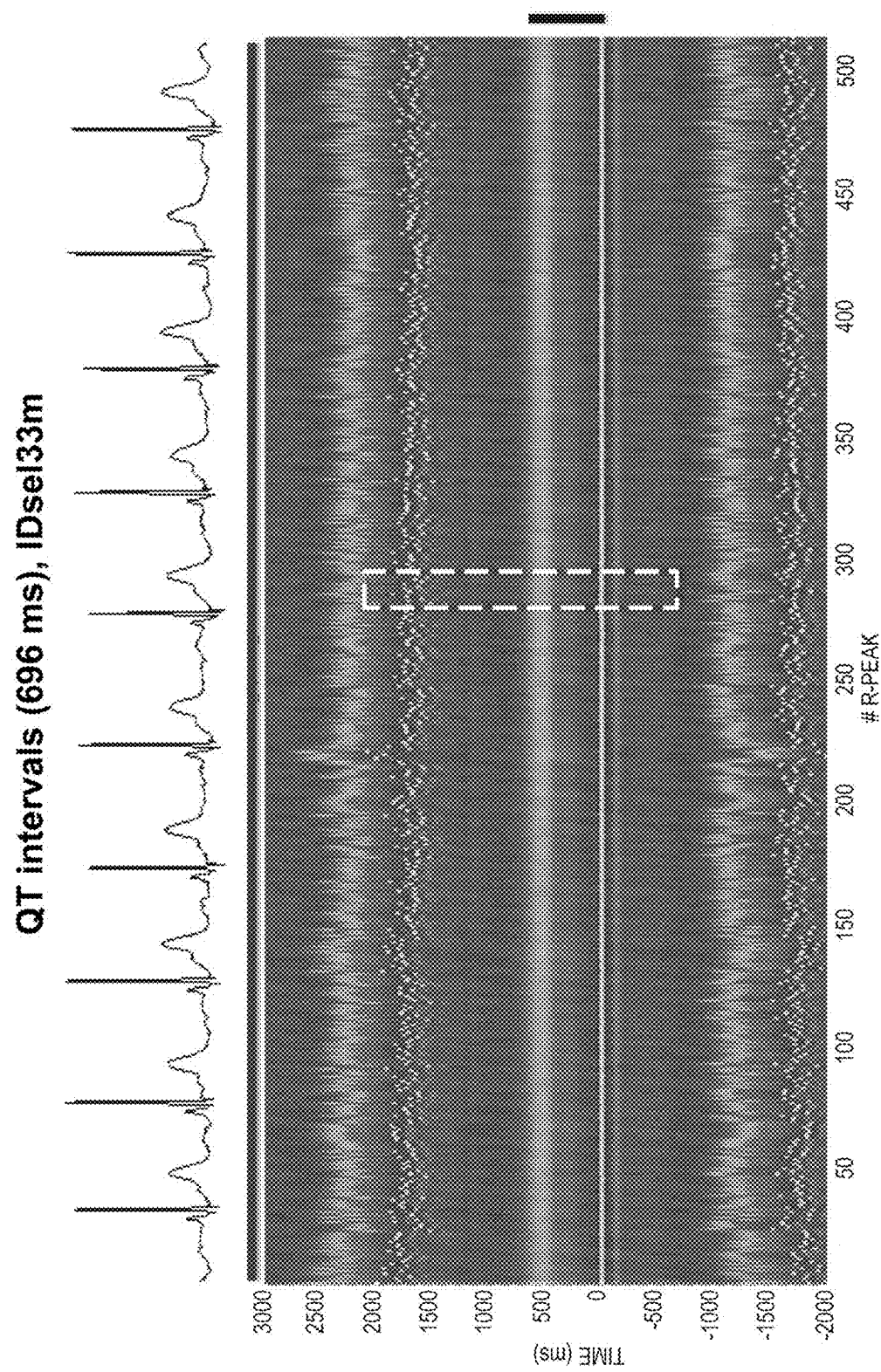
Figure 11J:
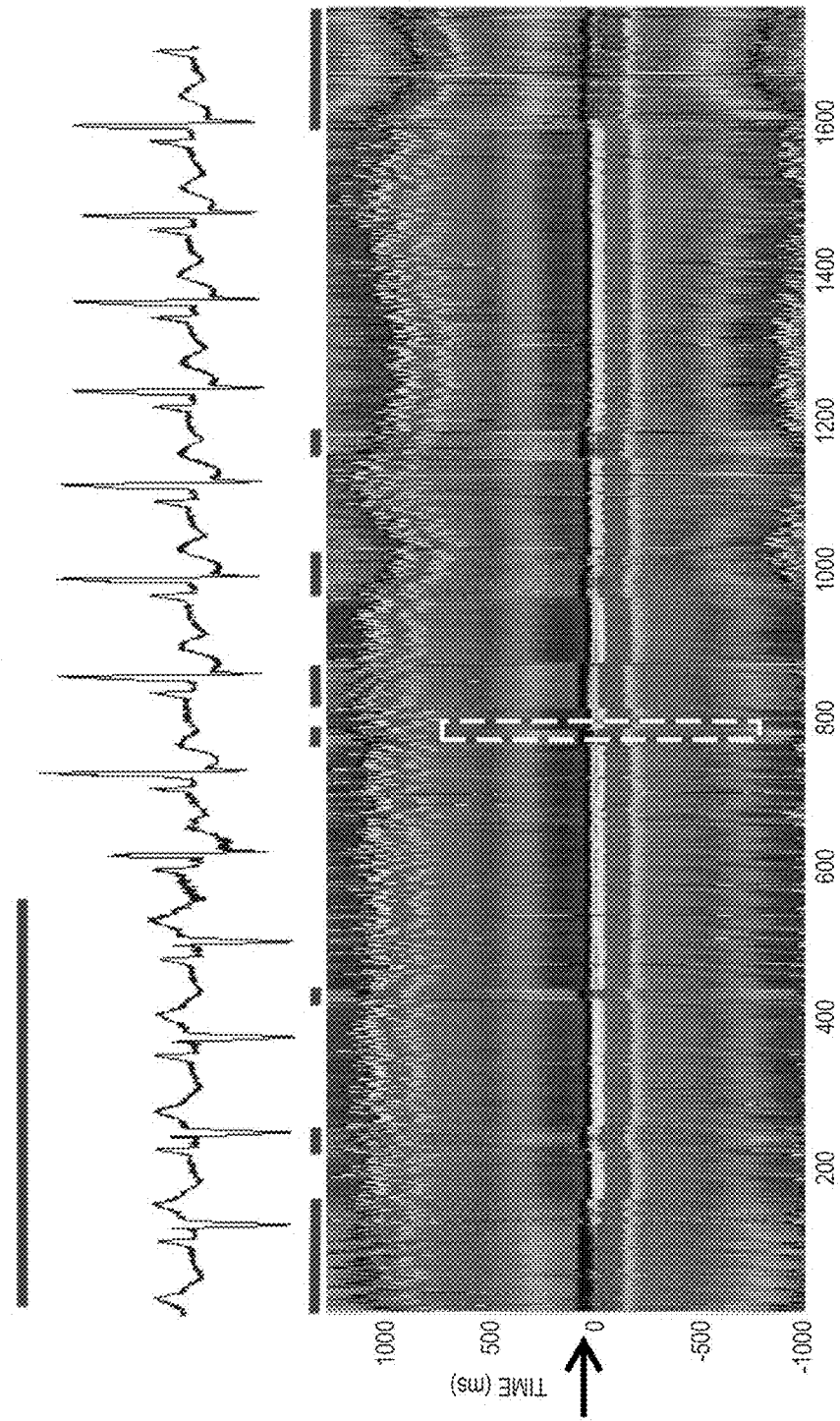
Figure 11K:
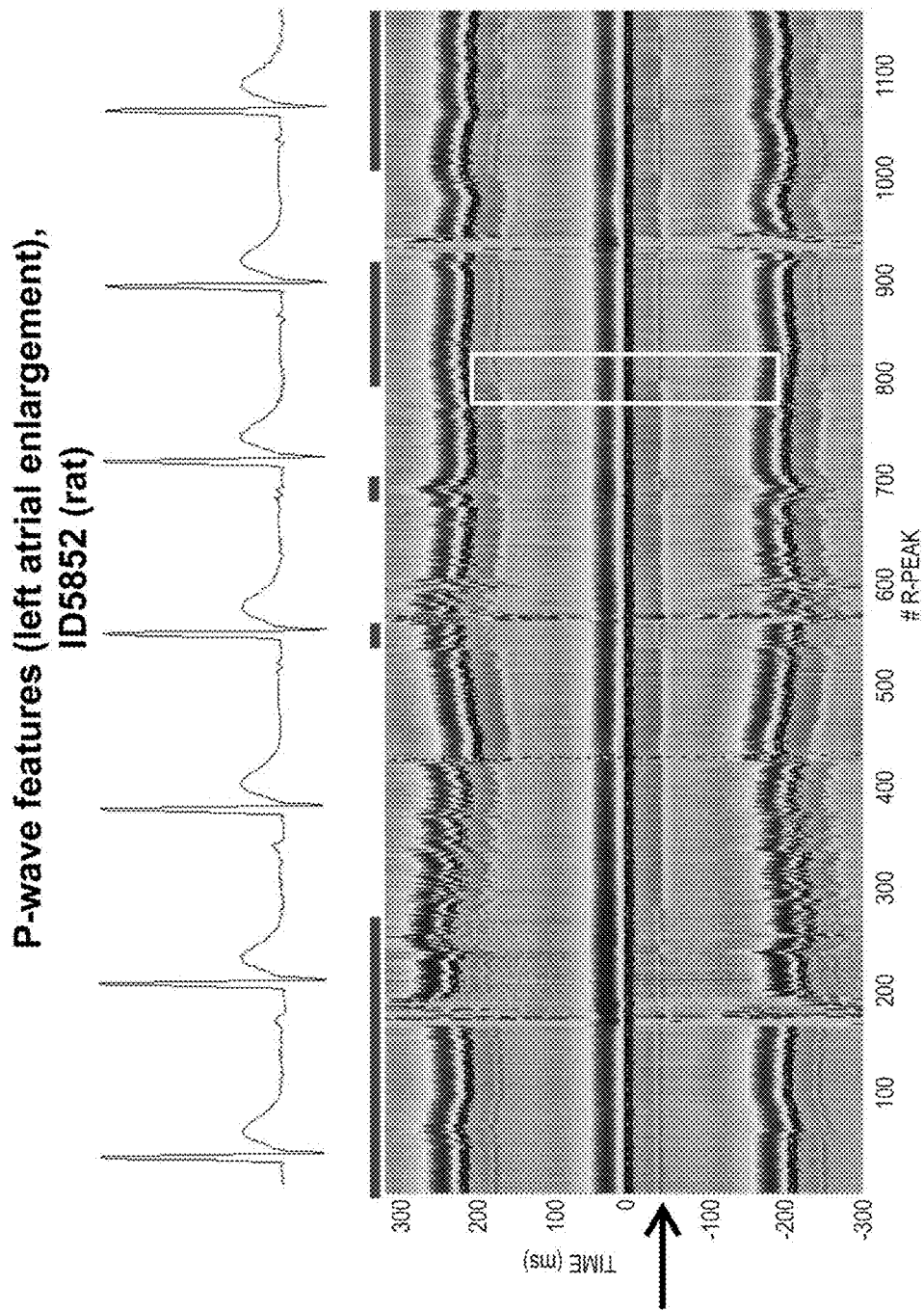

FIG. 11A illustrates long EKG signals displayed as a generated time-complex matrix and at different numbers of total heart beats (for a rat): 9000 beats for the top plot, 900 beats for the middle plot, and 90 beats for the bottom plot. FIG. 11B illustrates a time-dependent change of an RR interval from 900 ms (or 67 beats per minute at the $1950^{th}$ beat) to 700 ms (or 86 beats per minute at the $2000^{th}$ beat) and automatically identified, for example by the system 700. FIG. 11C illustrates a left bundle branch block (left BBB) pattern. FIG. 11D illustrates a right bundle branch block (right BBB) pattern. FIG. 11E illustrates a WPW beats pattern. FIG. 11F illustrates an ST depression pattern. FIG. 11G illustrates an ST elevation −1 pattern. FIG. 11H illustrates an ST elevation −2 pattern. FIG. 11I illustrates a QT interval pattern. FIG. 11J illustrates a QRS feature pattern. FIG. 11K illustrates a P-wave feature pattern.

Figure 11L:
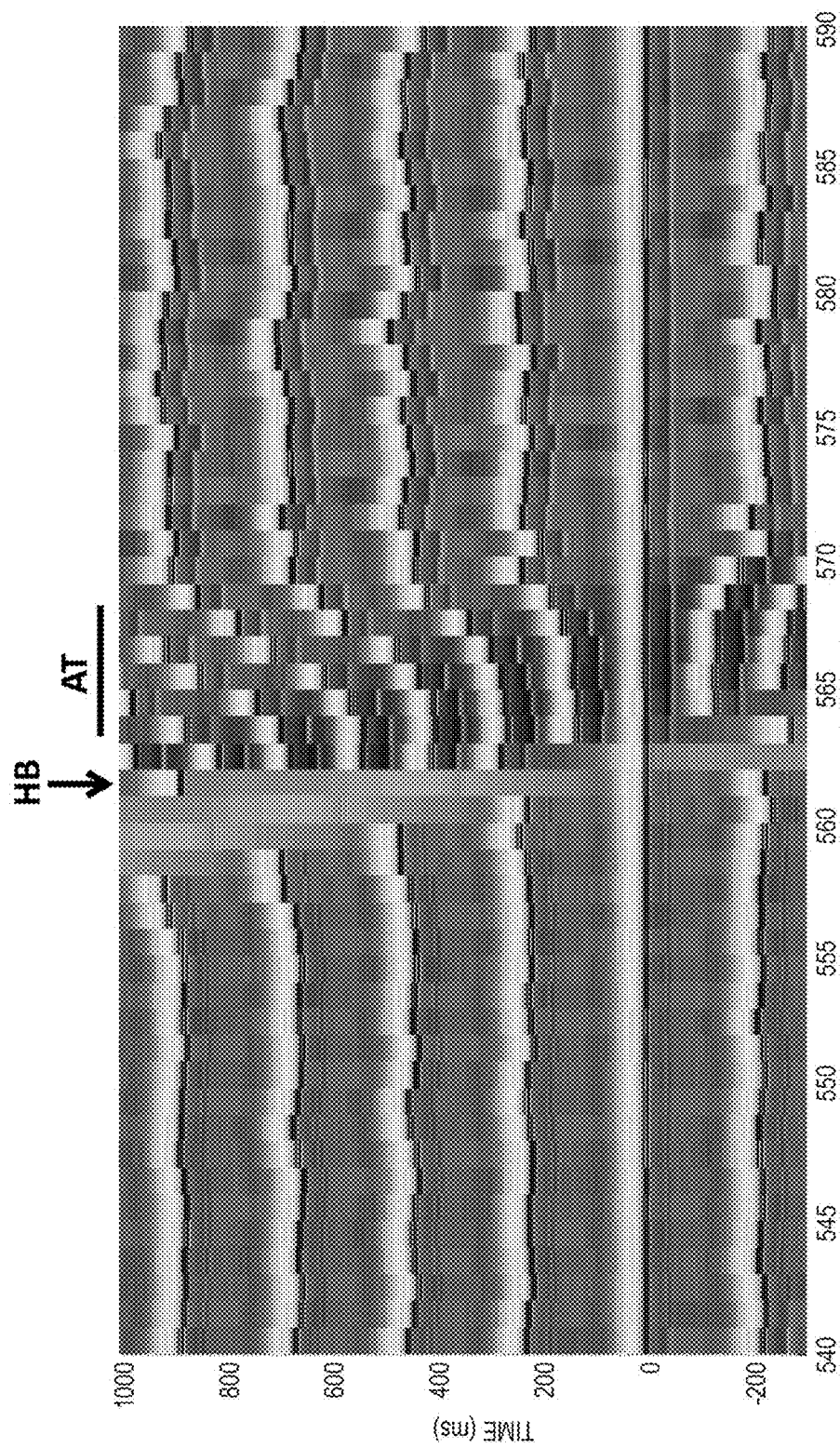
Figure 11M:
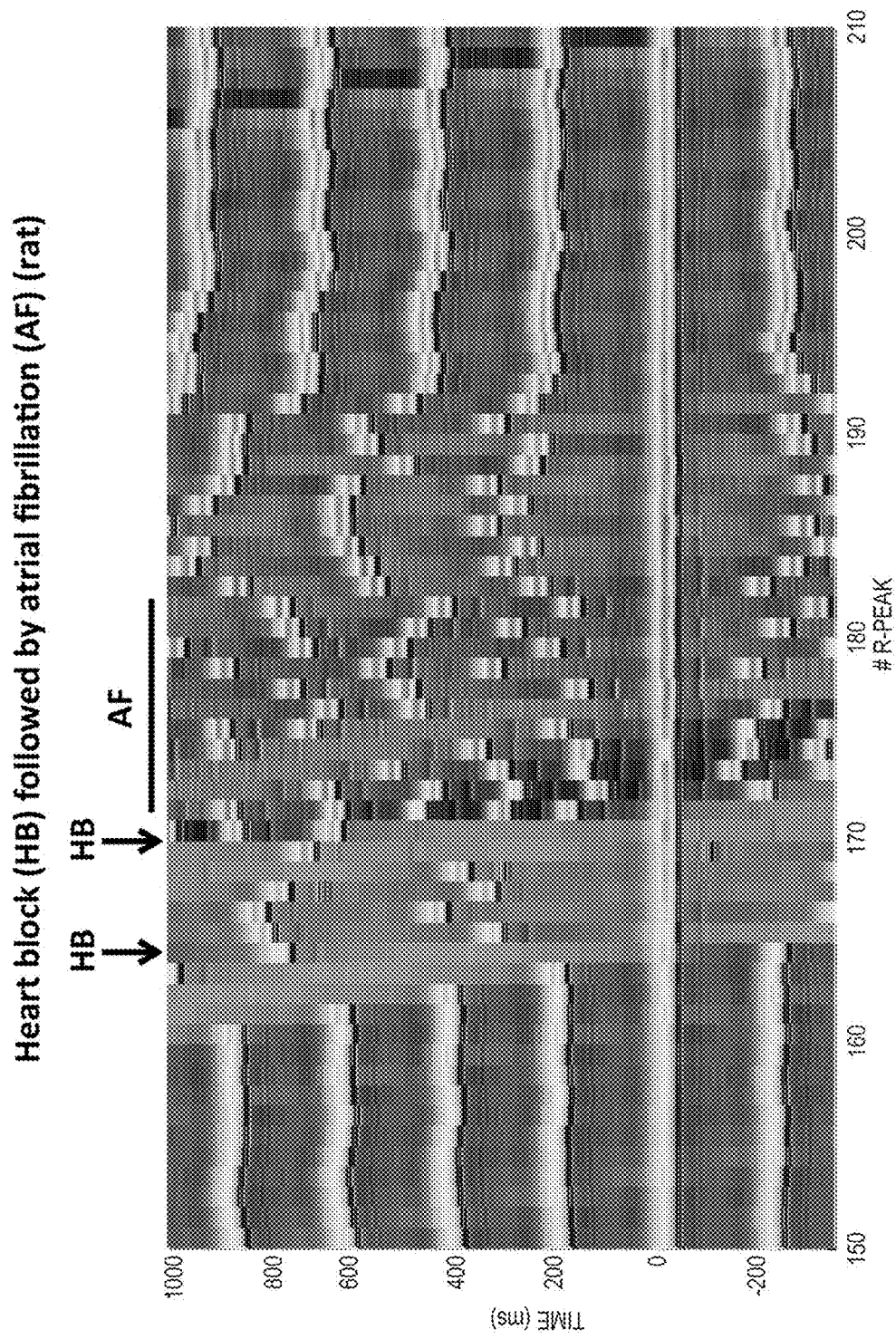
Figure 11N:
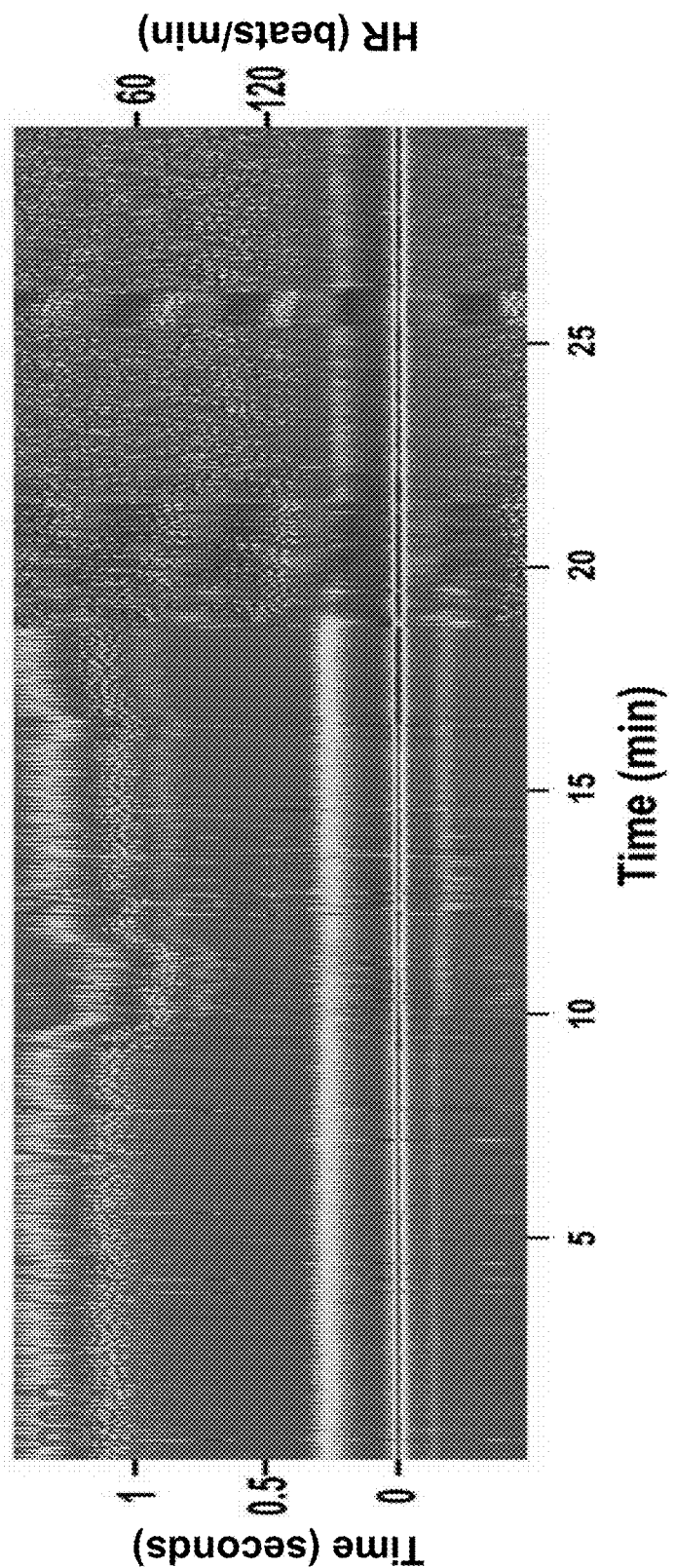

FIG. 11L illustrates a precursor pattern automatically identified by applying a precursor rule from the module 718. FIG. 11L illustrates a heart block (HB) followed by a resulting atrial tachycardia (AT) condition. A health care professional may be flagged to the HB condition by an arrow followed by, in this example, the module 720 also indicating an identified AT condition. FIG. 11M indicates two automatically identified HB conditions, both automatically indicated on the matrix, followed by an atrial fibrillation (AF) condition. FIG. 11N indicates automatically detected sudden heart rate increase and PR elongation conditions, followed by an atrial fibrillation condition in a human patient.

Figure 12:
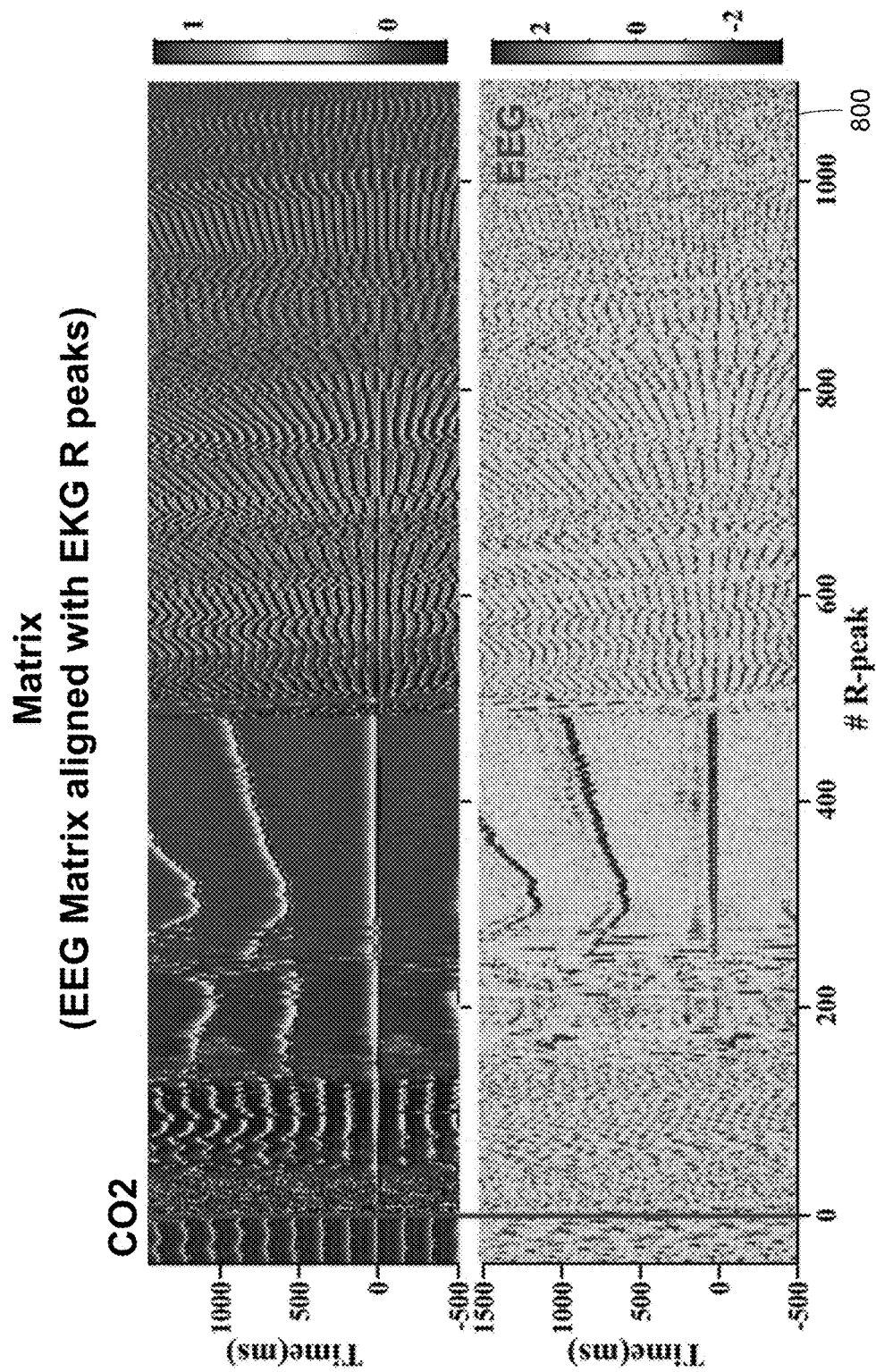
FIG. 12 illustrates an example time-complex matrix formed from analyzing and converting electroencephalography (EEG) signal data.

As noted, the present techniques may be applied to generate time-complex matrices of any number of input electrical signals. FIG. 12 illustrates an example matrix 800 generated from an EKG signal (top panel) and an EEG signal (bottom panel) from the same dying individual.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connects the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of the example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but also deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but also deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or an are employed to describe elements and components of the embodiments herein. This is done merely for convenience and to give a general sense of the description. This description, and the claims that follow, should be read to include one or at least one and the singular also includes the plural unless it is obvious that it is meant otherwise.

While the present invention has been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention.

The foregoing description is given for clearness of understanding; and no unnecessary limitations should be understood therefrom, as modifications within the scope of the invention may be apparent to those having ordinary skill in the art.

What is claimed:

1. A computer-implemented method of analyzing periodic electrical signal data of cardiac, muscular, or brain activity, wherein the electrical signal data is characterized by periodic deflection elements that collectively form a periodic signal complex, the method comprising:
   collecting the electrical signal data over a sampling window of time;
   automatically detecting, using a signal detection module, periodic localized peaks for one of the deflection elements from the electrical signal data and over the sampling window of time;
   determining, in the signal detection module, a relative peak value for each of the periodic localized peaks over the sampling window of time;
   transforming, using a matrix generating module, the electrical signal data into a time-complex matrix, the time-complex matrix characterized by alignment of each of the periodic localized peaks at a zero time level, wherein the respective relative peak values for the periodic localized peaks is represented by an intensity scale at the zero time level, and wherein the time-complex matrix is characterized by representing changes in the temporal spacing and intensities of the periodic signal complexes over the sampling window; and
   displaying the time-complex matrix as either a horizontal time progression or a vertical time progression plot.

2. The method of claim 1, wherein the periodic electrical signal data is selected from one of electrocardiogram (EKG) data, electromyography (EMG) data, and electroencephalography (EEG) data.

3. The method of claim 2, wherein the periodic electrical signal data is EKG data, and wherein the periodic signal complex is a QRS complex comprising, as the periodic deflection elements, P elements, Q elements, R elements, S elements, and T elements.

4. The method of claim 3, wherein automatically detecting periodic localized peaks for one of the deflection elements comprises:
   automatically detecting, using the signal detection module, R element peaks in the EKG data; and
   performing a validation on the R elements peaks to identify and correct any mis-detected R element peaks in the EKG data.

5. The method of claim 4, wherein transforming the electrical signal data into the time-complex matrix comprises:
   defining for each of the R element peaks in the EKG data an analysis window comprising the periodic complex producing the R element peak, at least one periodic complex preceding the periodic complex producing the R element peak, and at least one periodic complex succeeding the periodic complex producing the R element peak;
   forming the time-complex matrix by aligning the R element peaks at the zero time level over the sampling window; and
   displaying the time-complex matrix with the plurality of defined analysis windows extending (i) vertically in time to form the vertical time progression plot or (ii) horizontally in time to form the horizontal time progression plot.

6. The method of claim 1, further comprising:
   analyzing the time-complex matrix to identify patterns in the periodic deflection elements over the sampling window; and
   from the analysis of the time-complex matrix, automatically detecting a pattern indicative of one or more of an arrhythmia, a precursor to an arrhythmia, a cardiac event, and/or a precursor to a cardiac event, and wherein displaying the time-complex matrix comprises optionally displaying the detected pattern.

7. The method of claim 6, the method comprising automatically detecting the pattern indicative of at least one of atrial premature contraction (APC), aberrated APC, blocked APC, supraventricular tachycardia, atrial flutter, atrial fibrillation, junctional tachycardia, premature ventricular contraction (PVC), interpolated PVC, ventricular bigeminy, ventricular trigeminy, ventricular couplets, ventricular tachycardia, 2nd degree (Mobitz I and Mobitz II) heart block, 3rd degree (or complete) heart block, heart block followed by atrial tachycardia (AT), and heart block followed by atrial fibrillation (AF).

8. The method of claim 6, wherein the periodic electrical signal data is EKG data, and wherein the periodic signal complex is a QRS complex comprising, as the periodic deflection elements, P elements, Q elements, R elements, S elements, and T elements, wherein the method comprises automatically detecting the pattern indicative of at least one of RR interval changes, left bundle branch blockage, right bundle branch blockage, ST depression, ST elevation, QT interval changes, QRS interval changes, PR interval changes, split P-waves, and widened QRS bases indicative of Wolff-Parkinson-White heart beats.

9. The method of claim 1, wherein the time-complex matrix is characterized by representing changes in the temporal spacing and intensities of the periodic deflection elements over the sampling window.

10. The method of claim 1, wherein the intensity scale is a heat map.

11. A system comprising:
   a processor and a memory, the memory storing instructions that when executed by the processor, cause the processor to:
   collect electrical signal data over a sampling window of time, wherein the electrical signal data is data of cardiac, muscular, or brain activity, and wherein the electrical signal data is characterized by periodic deflection elements that collectively form a periodic signal complex;

detect periodic localized peaks for one of the deflection elements from the electrical signal data and over the sampling window of time;

determine a relative peak value for each of the periodic localized peaks over the sampling window of time;

transform the electrical signal data into a time-complex matrix, the time-complex matrix characterized by alignment of each of the periodic localized peaks at a zero time level, wherein the respective relative peak values for the periodic localized peaks is represented by an intensity scale at the zero time level, and wherein the time-complex matrix is characterized by representing changes in the temporal spacing and intensities of the periodic signal complexes over the sampling window; and display the time-complex matrix as either a horizontal time progression or a vertical time progression plot.

12. The system of claim 11, wherein the periodic electrical signal data is selected from one of electrocardiogram (EKG) data, electromyography (EMG) data, and electroencephalography (EEG) data.

13. The system of claim 12, wherein the periodic electrical signal data is EKG data, and wherein the periodic signal complex is a QRS complex comprising, as the periodic deflection elements, P elements, Q elements, R elements, S elements, and T elements.

14. The system of claim 13, wherein the instructions to detect periodic localized peaks for one of the deflection elements include instructions to:

detect R element peaks in the EKG data; and perform a validation on the R elements peaks to identify and correct any mis-detected R element peaks in the EKG data.

15. The system of claim 14, wherein the instructions to transform the electrical signal data into the time-complex matrix include instructions to:

define for each of the R element peaks in the EKG data an analysis window comprising the periodic complex producing the R element peak, at least one periodic complex preceding the periodic complex producing the R element peak, and at least one periodic complex succeeding the periodic complex producing the R element peak;

form the time-complex matrix by aligning the R element peaks at the zero time level over the sampling window; and display the time-complex matrix with the plurality of defined analysis windows extending (i) vertically in time to form the vertical time progression plot or (ii) horizontally in time to form the horizontal time progression plot.

16. The system of claim 11, wherein the memory stores instructions that when executed by the processor, cause the processor to:

analyze the time-complex matrix to identify patterns in the periodic deflection elements over the sampling window; and from the analysis of the time-complex matrix, detect a pattern indicative of one or more of an arrhythmia, a precursor to an arrhythmia, a cardiac event, and/or a precursor to a cardiac event.

17. The system of claim 16, wherein the instructions detect the pattern indicative of one or more of an arrhythmia, a precursor to an arrhythmia, a cardiac event, and/or a precursor to a cardiac event comprise instructions to identify a pattern indicative of at least one of atrial premature contraction (APC), aberrated APC, blocked APC, supraventricular tachycardia, atrial flutter, atrial fibrillation, junctional tachycardia, premature ventricular contraction (PVC), interpolated PVC, ventricular bigeminy, ventricular trigeminy, ventricular couplets, ventricular tachycardia, 2nd degree (Mobitz I and Mobitz II) heart block, 3rd degree (or complete) heart block, heart block followed by atrial tachycardia (AT), and heart block.

18. The system of claim 16, wherein the periodic electrical signal data is EKG data, and wherein the periodic signal complex is a QRS complex comprising, as the periodic deflection elements, P elements, Q elements, R elements, S elements, and T elements, wherein the method comprises automatically detecting the pattern indicative of at least one of RR interval changes, left bundle branch blockage, right bundle branch blockage, ST depression, ST elevation, QT interval changes, QRS interval changes, PR interval changes, split P-waves, and widened QRS bases indicative of Wolff-Parkinson-White heart beats.

19. The system of claim 11, wherein the time-complex matrix is characterized by representing changes in the temporal spacing and intensities of the periodic deflection elements over the sampling window.

\* \* \* \* \*